US006653321B1

United States Patent
Spevak et al.

(10) Patent No.: US 6,653,321 B1
(45) Date of Patent: Nov. 25, 2003

(54) NAPHTHYLSULFONIC ACIDS AND RELATED COMPOUNDS AS GLUCOSE UPTAKE AGONISTS

(75) Inventors: Wayne R. Spevak, Albany, CA (US); Songyuan Shi, Fremont, CA (US); Prasad V. V. S. V. Manchem, South San Francisco, CA (US); Michael R. Kozlowski, Palo Alto, CA (US); Steven R. Schow, Redwood Shores, CA (US); Robert T. Lum, Palo Alto, CA (US); Louise Robinson, San Carlos, CA (US); Jeong Weon Park, Emeryville, CA (US)

(73) Assignee: Telik, Inc., Palo Alto, CA (US)

( * ) Notice: Subject to any disclaimer, the term of this patent is extended or adjusted under 35 U.S.C. 154(b) by 0 days.

(21) Appl. No.: 09/628,206
(22) Filed: Jul. 28, 2000

Related U.S. Application Data

(60) Provisional application No. 60/146,444, filed on Jul. 29, 1999.

(51) Int. Cl.$^7$ .................. A61K 31/50; A61K 31/545; C07D 211/66; C07D 232/02; C07C 239/00
(52) U.S. Cl. .................. 514/307; 514/256; 514/311; 514/315; 514/319; 514/332; 514/357; 514/365; 514/374; 514/385; 514/415; 514/428; 514/438; 514/447; 514/451; 514/459; 514/461; 514/471; 514/521; 514/503; 514/568; 514/576; 514/613; 514/615; 514/619; 514/620; 544/238; 544/239; 544/240; 544/241; 544/242; 544/333; 544/334; 544/335; 544/336; 546/139; 546/146; 546/149; 546/152; 546/157; 546/162; 546/174; 546/175; 546/192; 546/195; 546/205; 546/206; 546/246; 546/247; 546/248; 548/146; 548/215; 548/233; 548/300.1; 548/326.5; 548/348.1; 548/349.1; 548/350.1; 548/469; 548/566; 549/139; 549/146; 549/149; 549/152; 549/157; 549/162; 549/174; 549/175; 549/192; 549/195; 549/205; 549/206; 549/246; 549/247; 549/248; 558/17; 562/54; 564/162; 564/163; 564/165; 564/169; 564/180; 564/185

(58) Field of Search .................. 562/54; 558/17; 564/185, 166, 162, 163, 169, 180; 546/139, 146, 149, 152, 159, 162, 174, 175, 192, 195, 246, 247, 248, 205, 206; 544/238, 239, 240, 241, 242, 333, 334, 335, 336; 548/146, 215, 233, 300.1, 326.5, 348.1, 349.1, 350.1, 469, 566; 549/29, 68, 74, 75, 76, 77, 356, 424, 429, 462, 480, 491, 496, 497, 499, 501; 514/247, 256, 311, 315, 319, 332, 357, 365, 374, 385, 415, 428, 568, 576, 613, 615, 619, 620, 438, 447, 451, 459, 461, 471, 521, 523

(56) References Cited

U.S. PATENT DOCUMENTS 3,716,368 A 2/1973 Froehlich et al. .............. 96/99

(List continued on next page.)

FOREIGN PATENT DOCUMENTS

DE 2 216 592 4/1972

(List continued on next page.)

OTHER PUBLICATIONS

Database Chemabs "OnLine" Chemical Abstract Service, Columbus Ohio, US; STN, CAPLUS accession No. 1988:436172, XP002151699, abstract of YA. YA. Aleksandrovskii: *Vopr. Med. Khim.*, vol. 34, No. 3, 1988, pp. 7–25.

(List continued on next page.)

*Primary Examiner*—Alan L. Rotman
*Assistant Examiner*—Raymond Covington
(74) *Attorney, Agent, or Firm*—Heller, Ehrman, White & McAuliffe, LLP

(57) ABSTRACT

Methods for treating conditions associated with hyperglycemia, especially Type II diabetes, with novel naphthylsulfonic acids and related compounds. These compounds, as single stereoisomers or mixtures of stereoisomers, or their pharmaceutically acceptable salts, are useful in methods of stimulating the kinase activity of the insulin receptor, enhancing the activation of the insulin receptor by insulin, and stimulating the uptake of glucose into cells. A variety of antidiabetic compounds and pharmaceutical compositions comprising the antidiabetic compounds are also disclosed.

30 Claims, 3 Drawing Sheets

U.S. PATENT DOCUMENTS

| | | | |
|---|---|---|---|
| 4,051,176 A | 9/1977 | Bernstein et al. | 260/506 |
| 4,102,917 A * | 7/1978 | Conrow et al. | 558/17 |
| 4,108,890 A * | 8/1978 | Bernstein et al. | 562/54 |
| 4,118,232 A | 10/1978 | Piller et al. | 96/99 |
| 4,120,891 A | 10/1978 | Poletto et al. | 260/506 |
| 4,129,591 A | 12/1978 | Bernstein et al. | 260/506 |
| 4,132,730 A * | 1/1979 | Conrow et al. | 562/54 |
| 4,229,371 A * | 10/1980 | Conrow et al. | 562/54 |
| 5,589,510 A | 12/1996 | Ono et al. | 514/590 |

FOREIGN PATENT DOCUMENTS

| | | |
|---|---|---|
| DE | 195 21 589 | 12/1996 |
| FR | 1 578 556 | 8/1969 |
| WO | 92/22610 | 12/1992 |
| WO | 98/32017 | 7/1998 |

OTHER PUBLICATIONS

S. Budavari, et al., "The Merck Index", Twelfth Edition (1996), pp. 1541, entry 9181, Suramin sodium.

* cited by examiner

Effect of Compound 8 on 3T3 HIR cells

NAPHTHYLSULFONIC ACIDS AND RELATED COMPOUNDS AS GLUCOSE UPTAKE AGONISTS

CROSS-REFERENCE TO RELATED APPLICATIONS

This application claims the priority under 35 USC 119(e) of Provisional Application No. 60/146,444, filed Jul. 29, 1999, entitled NOVEL NAPHTHYLSULFONIC ACIDS AND RELATED COMPOUNDS AS GLUCOSE UPTAKE ENHANCERS. This applications, in its entirety, is incorporated herein by reference.

BACKGROUND OF THE INVENTION (a) Field of the Invention

The present invention relates to methods, pharmaceutical compositions, and compounds for enhancing insulin-dependent glucose uptake. The compounds of the invention activate the insulin receptor kinase, leading to an increased sensitivity to insulin and an increase in glucose uptake. The invention relates in particular to the use of the compounds in methods for the treatment of humans with hyperglycemia, and especially for the treatment of Type II diabetes.

(b) Description of Related Art

Among the many functions performed by peptide and protein hormones in metabolism is the ability to interact with receptors with high specificity. The insulin receptor is present on virtually all cells and at high concentrations on the cells for the liver, skeletal muscles, and adipose tissue. Stimulation of the insulin receptor with insulin is an essential element in carbohydrate metabolism and storage.

Diabetics either lack sufficient endogenous secretion of the insulin hormone (Type I) or have an insulin receptor-mediated signaling pathway that is resistant to endogenous or exogenous insulin (Type II, or non-insulin-dependent diabetes mellitus (NIDDM)). Type II diabetes is the most common form of diabetes, affecting about 5% of individuals in the industrialized nations. In Type II diabetics, major insulin-responsive tissues such as liver, skeletal muscle and fat exhibit the insulin resistance (Haring and Mehnert, *Diabetologia* 36:176–182 (1993); Haring et al., *Diabetologia*, 37 Suppl 2:S149–54 (1994)). The resistance to insulin in Type II diabetes is complex and likely multi-factorial but appears to be caused by an impaired signal from the insulin receptor to the glucose transport system and to glycogen synthase. Impairment of the insulin receptor kinase has been implicated in the pathogenesis of this signaling defect. Insulin resistance is also found in many non-diabetic individuals, and may be an underlying etiologic factor in the development of the disease (Reaven, *Diabetes*, 37:1595–1607 (1988)).

Considerable information is known concerning the insulin receptor itself. The receptor consists of four separate sub-units consisting of two identical β and two identical β chains. The β subunits contain a tyrosine kinase activity and the ATP binding sites. The insulin receptor is activated by autophosphorylation of key tyrosine residues in its cytoplasmic tyrosine kinase domain. This autophosphorylation is required for subsequent activity of the insulin receptor. The autophosphorylation stabilizes the activated receptor kinase resulting in a phosphorylation cascade involving intracellular signaling proteins.

At present there are limited pharmacologic approaches to treatment of Type II diabetes. Insulin is currently used as a treatment, but is disadvantageous because it must be injected and because its extreme potency requires careful titration of dose. Although several peptide analogs of insulin have been described, none with a molecular weight below about 5000 Daltons retains activity. Some peptides which interact with sites on the β-subunit of the insulin receptor have shown enhancement of the activity of insulin on its receptor (Kole et al., *J. Biol Chem.*, 271:31619–31626 (1996); Kasuya et al., *Biochem. Biophys. Res. Commun.*, 200:777–83 (1994)). Kohanski and others have reported on a variety of polycationic species that generate a basal effect, but do little to enhance insulin action (Kohanski, *J. Biol. Chem.*, 264:20984–91 (1989); Xu et al., *Biochemistry* 30:11811–19 (1991). These peptides apparently act on the cytoplasmic kinase domain of the insulin receptor.

In addition, certain non-peptide components have been found to enhance the agonist properties of peptide hormones, but none appear to act directly on the insulin receptor kinase. For instance, the ability of thiazolidinediones, such as pioglitazone, to enhance adipocyte differentiation has been described (Kletzien, et al., *Mol. Pharmacol.*, 41:393 (1992)). These thiazolidinediones represent a class of potential anti-diabetic compounds that enhance the response of target tissues to insulin (Kobayashi, *Diabetes*, 41:476 (1992)). The thiazolidinediones act at an unknown site downstream from the insulin receptor itself and do not have a direct effect on the insulin receptor kinase. Other anti-diabetic agents currently in use include both insulin secretagogues (such as the sulfonylureas) and biguanides (such as metformin) that inhibit hepatic glucose output. To date, non-peptide substances which can mimic the activating effect of insulin on the insulin receptor have eluded discovery.

A variety of polyanionic sulfonic acid derivatives including suramin, azo dyes and related compounds are known in the art and have been established as potential therapeutics for a variety of disease indications. Suramin, described in 1917, is a polysulfonic acid that has been extensively researched (Dressel, *J. Chem. Ed.*, 38:585 (1961); Dressel, *J. Chem. Ed.*, 39:320 (1962)). It has therapeutic uses as an anthelmintic and antiprotozoal. More recently, it has been described as an inhibitor to reverse transcriptase in certain avian and murine retroviruses (De Clercq, *Cancer Letters*, 8:9 (1979); Mitsuya et al., *Science*, 226:172 (1984)). Large numbers of compounds relating to suramin exist. Most of the suramin analogs which have been reported have multiple sulfonic acid functionality on each aryl ring. Recent studies indicate that polyanionic suramin analogs have anti-angiogenic, antiproliferative activity, and anti-viral activity (Gagliardi et al., *Cancer Chemother. Pharmacol.*, 41:117 (1988); Doukas et al., *Cancer Res.*, 55: 5161 (1995); Mohan et al., *Antiviral Chem.*, 2:215 (1991)). A number of other bisnaphthylsulfonic acids have been described in the patent literature as complement inhibitors (U.S. Pat. No. 4,132,730, U.S. Pat. No. 4,129,591, U.S. Pat. No. 4,120,891, U.S. Pat. No. 4,102,917, U.S. Pat. No. 4,051,176). Additionally, there are a number of azo dye patents (DE 19521589, U.S. Pat. No. 3,716,368, DE 2216592, FR 1578556) which disclose polysulfonated naphthalene azo compounds. However, none of the suramin analogs or azo dyes have been suggested to be useful in the treatment of hyperglycemia or diabetes.

SUMMARY OF THE INVENTION

This invention is directed to pharmaceutical compositions comprising naphthalene sulfonic acids and related compounds which enhance glucose uptake into cells, to the naphthalene sulfonic acids and related compounds, and to methods for enhancing glucose uptake in mammals using these pharmaceutical compositions and compounds.

In one aspect, this invention is directed to pharmaceutical compositions comprising (i) a pharmaceutically acceptable carrier and (ii) as an active ingredient, a compound of formula I:

Formula I

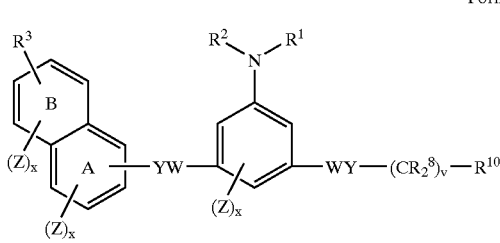

where:

- $R^1$ and $R^2$ are, independently, hydrogen, alkyl, substituted alkyl, aryl, substituted aryl, —C(O)$R^4$, —C(O)O$R^4$, —C(O)N$R^4R^5$, —S(O)$_2R^4$, —S(O)$_2$O$R^4$, heteroaryl, substituted heteroaryl, heterocyclyl, substituted heterocyclyl, aryl(lower)alkyl, substituted aryl(lower)alkyl, heteroaryl(lower)alkyl, substituted heteroaryl (lower)alkyl, or lower alkenyl, or $R^1$ and $R^2$ together with the conjoining nitrogen are $C_3$–$C_9$ heteroaryl, $C_3$–$C_5$ heterocyclyl, or both $R^1$ and $R^2$ are oxygen and together with the conjoining nitrogen forming —NO$_2$,
- $R^3$ is a substituent on the B ring and is —SO$_2$O$R^6$, —C(O)O$R^6$, —SO$_2$N$R^6{}_2$, —C(O)N$R^6{}_2$ or tetrazolyl;
- each $R^4$ and $R^5$ is, independently, hydrogen, alkyl, substituted alkyl, aryl, substituted aryl, aryl(lower)alkyl, substituted aryl(lower)alkyl, substituted heteroaryl, heteroaryl, heteroaryl(lower)alkyl, substituted heteroaryl(lower)alkyl, heterocyclyl, substituted heterocyclyl, or lower alkenyl,
- each $R^6$ and $R^7$ is, independently, hydrogen or lower alkyl,
- each $R^8$ is, independently, hydrogen, lower alkyl, substituted lower alkyl, aryl(lower)alkyl, substituted aryl(lower)alkyl, substituted heteroaryl, heteroaryl, heteroaryl(lower)alkyl, substituted heteroaryl(lower) alkyl, heterocyclyl, substituted heterocyclyl, lower alkenyl, nitro, halo, cyano, —O$R^9$, —S$R^9$, —C(O)$R^9$, —OC(O)$R^9$, —C(O)O$R^9$, —N$R^9{}_2$, —C(O)N$R^9{}_2$, —N$R^9$C(O)$R^9$, —OSO$_2R^9$, —SO$_2$O$R^9$, —SO$_2$N$R^9{}_2$, or —N$R^9$SO$_2R^9$,
- each $R^9$ is, independently, hydrogen, lower alkyl, substituted lower alkyl, aryl, substituted aryl, heteroaryl, substituted heteroaryl, heteroaryl(lower)alkyl, substituted heteroaryl(lower)alkyl, heterocyclyl, substituted heterocyclyl, aryl(lower)alkyl, or substituted aryl (lower)alkyl,
- $R^{10}$ is aryl, substituted aryl, heteroaryl, or substituted heteroaryl,
- each linker —WY— between the naphthyl and phenyl intersects the A ring on the naphthyl and is, independently, —C(O)N$R^7$—, —N$R^7$C(O)—, —C(O) O—, —OC(O)—, —CH=CH—, —N$R^7$CH$_2$—, —CH$_2$N$R^7$—, —N$R^7$C(O)N$R^7$—, —N$R^7$C(O)O—, —OC(O)N$R^7$—, —N$R^7$SO$_2$O—, —OSO$_2$N$R^7$—, —OC(O)O—, —SO$_2$N$R^7$—, —N$R^7$SO$_2$—, —OSO$_2$—, or —SO$_2$O—,
- each Z is a non-interfering substituent, and
- each x and v is, independently, 0, 1, 2 or 3, as a single stereoisomer or mixture of stereoisomers, or a pharmaceutically acceptable salt thereof.

In a second aspect, the invention provides a method of stimulating the kinase activity of the insulin receptor comprising contacting the insulin receptor, or the kinase portion thereof, with a compound of the first aspect of this invention, in an amount sufficient to stimulate the kinase activity of the insulin receptor.

In a third aspect, this invention provides a method of activating the insulin receptor or enhancing the activation of the insulin receptor by insulin comprising contacting the insulin receptor, or the kinase portion thereof, with a compound of the first aspect of this invention, in an amount sufficient to activate the insulin receptor or enhance insulin's activation of the insulin receptor. Enhancement of insulin's ability to activate its receptor in a mammal may be effected by administering the compound of the first aspect of this invention to the mammal.

In a fourth aspect, the invention provides the use of a compound of the first aspect of this invention in a method of stimulating the uptake of glucose into cells which display the insulin receptor. This method of stimulating the uptake of glucose into cells which display the insulin receptor comprises contacting the cells in the presence of insulin with a compound of the first aspect of this invention in an amount sufficient to stimulate the uptake of glucose into the cells. The uptake of glucose into cells in a mammal may be effected by administering the compound of the first aspect of this invention to the mammal.

Other aspects of the invention are directed to the use of a compound of the first aspect of this invention in the treatment of hyperglycemia, type I diabetes, or type II diabetes in a mammal, such as a human. These methods of treatment all comprise the step of administering a therapeutically effective amount of the a compound of the first aspect of this invention to the mammal. Optionally, the methods of treatment may also comprise administering insulin to the mammal.

Another aspect of the invention is directed to compounds of formula I, where: each $R^4$ and $R^5$ is, independently, hydrogen, alkyl, $R^{11}$-substituted alkyl, aryl, $R^{11}$-substituted aryl, aryl(lower)alkyl, $R^{11}$-substituted aryl(lower)alkyl, $R^{11}$-substituted heteroaryl, heteroaryl, heteroaryl(lower)alkyl, substituted $R^{11}$-substituted heteroaryl(lower)alkyl, heterocyclyl, $R^{11}$-substituted heterocyclyl, or lower alkenyl; each $R^{11}$ is, independently, aryl, substituted aryl, alkyl, substituted alkyl, substituted heteroaryl, heteroaryl, heterocyclyl, substituted heterocyclyl, lower alkenyl, nitro, halo, cyano, —O$R^{12}$, —S$R^{12}$, —C(O)$R^{12}$, —OC(O)$R^{12}$, —C(O)O$R^{12}$, —N$R^{12}{}_2$, —C(O)N$R^{13}{}_2$, —N$R^{12}$C(O)$R^{13}$, —OSO$_2R^{12}$, —SO$_2$O$R^{12}$, —SO$_2$N$R^{12}{}_2$, or —N$R^{12}$SO$_2R^{12}$; and each $R^{12}$ and $R^{13}$ is, independently, hydrogen, lower alkyl, substituted lower alkyl, aryl, substituted aryl, heteroaryl, substituted heteroaryl, heteroaryl(lower)alkyl, substituted heteroaryl(lower)alkyl, heterocyclyl, substituted heterocyclyl, aryl(lower)alkyl, or substituted aryl(lower) alkyl; provided that if $R^{10}$ is naphthyl, v is 0, and each —WY— is —C(O)N$R^7$— or —N$R^7$C(O)—, then (i) Z is not —SO$_2$OH; and (ii) if $R^1$ or $R^2$ is —C(O)N$R^4R^5$, then $R^{13}$ is neither aryl nor substituted aryl. Pharmaceutical compositions comprising a pharmaceutically acceptable carrier and these compounds of the invention as active ingredients are provided in still another aspect of the invention.

DETAILED DESCRIPTION OF THE INVENTION

(a) Definitions and General Parameters

Figure 1:
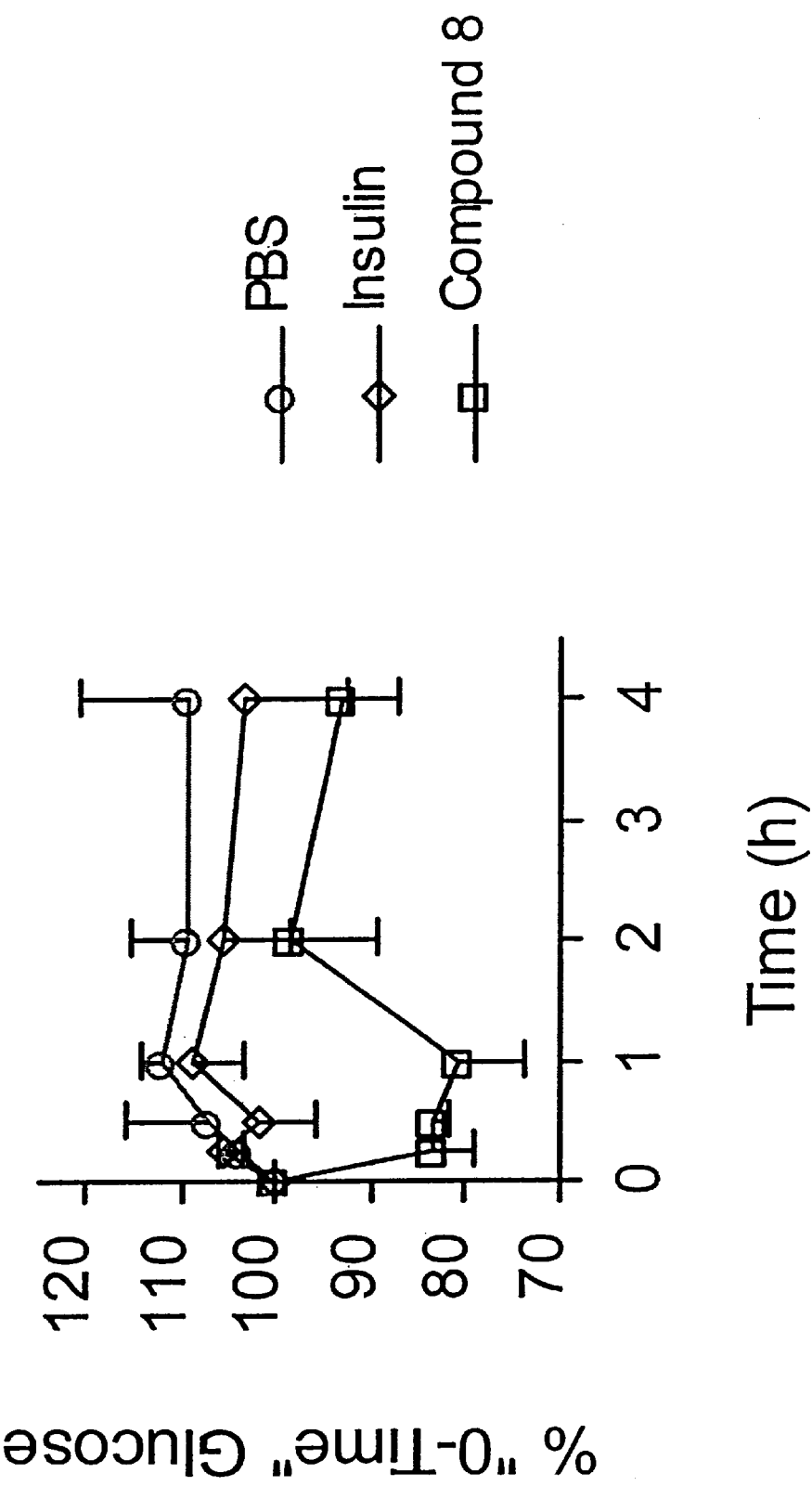
FIG. 1 shows the effect of a compound of the invention, compound 8, in combination with insulin on blood glucose levels in db/db mice.

"Alkyl", as in "alkyl" or "alkyloxy", means $C_1$–$C_{20}$ monovalent hydrocarbyl moiety which may be linear, branched, or cyclic. "Lower alkyl", as in "lower alkyl", "halo-lower alkyl", "aryl(lower)alkyl", or "heteroaryl (lower)alkyl", means a $C_1$–$C_{10}$ alkyl. The term "lower alkyl" includes such moieties as methyl, ethyl, isopropyl, propyl, butyl, isobutyl, sec-butyl, tert-butyl, pentyl, hexyl, cyclopentyl, cyclopropylmethyl, cyclohexyl, or cyclohexylmethyl. $C_1$–$C_6$ lower alkyls are preferred.

A "substituted alkyl" or "substituted lower alkyl" is an alkyl or lower alkyl, respectively, which is typically mono-, di-, or tri-substituted with a moiety such as aryl, R'-substituted aryl, heteroaryl, nitro, cyano, halo, —OR, —SR, —COR, —OC(O)R, —C(O)OR, —NR$_2$, —SO$_2$OR, —OSO$_2$R, —SO$_2$NR$_2$, —NRSO$_2$R, —CONR$_2$, or —NRCOR, where each R is, independently, hydrogen, lower alkyl, R'-substituted lower alkyl, aryl, R'-substituted aryl, heteroaryl, heteroaryl(lower)alkyl, R'-substituted aryl (lower)alkyl, or aryl(lower)alkyl and each R' is, independently, hydroxy, halo, lower alkyloxy, cyano, thio, nitro, lower alkyl, halo-lower alkyl, or amino. Substituted alkyls or substituted lower alkyls which are substituted with one to three of the substituents selected from the group consisting of cyano, halo, lower alkyloxy, thio, nitro, amino, or hydroxy are particularly preferred.

The term "halo-lower alkyl" means a lower alkyl substituted with one to three halo groups, and is further exemplified by such radicals as —CF$_3$, —CH$_2$CF$_3$ and —CH$_2$CCl$_3$.

"Aryl", as in "aryl", "aryloxy", and "aryl(lower)alkyl", means a radical derived from an aromatic hydrocarbon containing 6 to 20 ring carbon atoms, having a single ring (e.g., phenyl), or two or more condensed rings, preferably 2 to 3 condensed rings (e.g., naphthyl), or two or more aromatic rings, preferably 2 to 3 aromatic rings, which are linked by a single bond (e.g., biphenyl). The aryl is preferably $C_6$–$C_{16}$ and even more preferably, $C_6$ to $C_{14}$.

A "substituted aryl" is an aryl radical which is substituted, multiply or singly, with a moiety such as an alkyl, R'-substituted alkyl, halo, cyano, nitro, —SR, —OR, —COR, —OCOR, —SO$_2$OR, —OSO$_2$R, —SO$_2$NR$_2$, —NRSO$_2$R, —COOR, —NR$_2$, —CONR$_2$, or —NRCOR, where each R is, independently, hydrogen, lower alkyl, R'-substituted lower alkyl, aryl, R'-substituted aryl, heteroaryl, heteroaryl(lower)alkyl, aryl(lower)alkyl, or R'-substituted aryl(lower)alkyl and each R' is, independently hydroxy, halo, lower alkyloxy, cyano, thio, nitro, lower alkyl, halo-lower alkyl, or amino. A substituted aryl may be substituted from one to seven times with any combination of the radicals listed above. Preferably, however, the substituted aryl is mono-, di-, or tri-substituted. Especially preferred substituents on a substituted aryl are lower alkyl, halo-lower alkyl, halo, cyano, thio, nitro, amino, lower alkyloxy, or hydroxy. The radicals —SO$_2$OR, —SO$_2$NR$_2$, —COOR, and —CONR$_2$, where R is hydrogen or lower alkyl, are also especially preferred substituents of substituted aryls on the compounds of the present invention.

"Heteroaryl", as in heteroaryl and heteroaryl(lower)alkyl, means a radical derived from an aromatic hydrocarbon containing 5 to 14 ring atoms, 1 to 5 of which are hetero atoms chosen, independently, from N, O, or S, and includes monocyclic, condensed heterocyclic, and condensed carbocyclic and heterocyclic aromatic rings (e.g., thienyl, furyl, pyrrolyl, pyrimidinyl, isoxazolyl, oxazolyl, indolyl, isobenzofuranyl, purinyl, isoquinolyl, pteridinyl, imidazolyl, pyridyl, pyrazolyl, pyrazinyl, quinolyl, etc.).

A "substituted heteroaryl" may have from one to three substituents such as an alkyl, R'-substituted alkyl, halo, cyano, nitro, —SR, —OR, —COR, —OOCR, —SO$_2$OR, —OSO$_2$R, —SO$_2$NR$_2$, —NRSO$_2$R, —COOR, —NR$_2$, —CONR$_2$, or —NRCOR, where each R is independently hydrogen, lower alkyl, R'-substituted lower alkyl,aryl, R'-substituted aryl, heteroaryl, heteroaryl(lower)alkyl, aryl (lower)alkyl, or R'-substituted aryl(lower)alkyl and each R' is, independently, hydroxy, halo, lower alkyloxy, cyano, thio, nitro, lower alkyl, halo-lower alkyl, or amino. In addition, any two adjacent substituents on the heteroaryl may optionally together form a lower alkylenedioxy. Particularly preferred substituents on the substituted heteroaryl include hydroxy, halo, lower alkyloxy, cyano, thio, nitro, lower alkyl, halo-lower alkyl, halo-lower alkyl, or amino.

"Heterocyclyl" means a radical derived from an aliphatic, cyclic hydrocarbon containing 5 to 14 ring atoms, 1 to 5 of which are hetero atoms chosen, independently, from N, O, or S. Monocyclic rings (e.g., tetrahydrofuranyl, tetrahydropyranyl, piperidinyl, etc.) are preferred.

A "substituted heterocyclyl" may have from one to three substituents, preferably substituents like an alkyl, R'-substituted alkyl, halo, cyano, nitro, —SR, —OR, —COR, —OOCR, —SO$_2$OR, —OSO$_2$R, —SO$_2$NR$_2$, —NRSO$_2$R, —COOR, —NR$_2$, —CONR$_2$, or —NRCOR, where each R is, independently, hydrogen, lower alkyl, R'-substituted alkyl, aryl, R'-substituted aryl, heteroaryl, heteroaryl(lower)alkyl, aryl(lower)alkyl, or R'-substituted aryl(lower)alkyl and each R' is, independently hydroxy, halo, lower alkyloxy, cyano, thio, nitro, lower alkyl, halo-lower alkyl, or amino. Preferred substituents on a substituted heterocyclyl include lower alkyl, halo-lower alkyl, halo, cyano, thio, amino, lower alkyloxy, or hydroxy.

"Aryl(lower)alkyl" means a lower alkyl radical which is substituted with an aryl, as previously defined. A "substituted aryl(lower)alkyl" means an aryl(lower)alkyl radical having one to three substituents on the aryl portion or the alkyl portion of the radical, or both.

"Heteroaryl(lower)alkyl" means a lower alkyl radical which is substituted with a heteroaryl, as previously defined. A "substituted heteroaryl(lower)aryl" means a heteroaryl (lower)alkyl radical having one to three substituents on the heteroaryl portion or the alkyl portion of the radical, or both.

A "lower alkyloxy" means an —OR radical, where R is a lower alkyl.

"Lower alkenyl" means any branched or unbranched unsaturated $C_2$–$C_{10}$ group having the number of carbon atoms specified, or up to 10 carbon atoms if no limitation on the number of carbon atoms is specified; and having 1 or more double bonds in the group. Lower alkenyl is exemplified by ethenyl, propenyl, butenyl, pentenyl, and hexenyl, in their various isomeric forms, where the unsaturated bond(s) can be located anywhere in the group.

"Halo" means bromo, iodo, fluoro, or chloro.

A "non-interfering substituent" means a substituent which, when present on a given compound, does not substantially decrease or otherwise inhibit a particular, desired bioactivity of the compound, such as the ability of the compound to stimulate the kinase activity of the insulin receptor, to activate the insulin receptor, or to stimulate the uptake of glucose into cells displaying the insulin receptor. The presence of the non-interfering substituent should not detrimentally affect the bioactivity of the compound by more than about 30%. Preferably, the non-interfering substituent decreases the bioactivity of the compound by less than about 10%. Most preferably, the non-interfering substituent does not decrease the bioactivity of the compound to any detectable degree. However, the effect of the presence of the non-interfering substituent on the compound need not be neutral. For instance, the non-interfering substituent may optionally increase a particular bioactivity of the compound. Suitable non-interfering substituents include, but are not limited to, alkyl, substituted alkyl, cyano, halo, nitro, —SR, —OR, and —NR$_2$, where each R is, independently, hydrogen, lower alkyl, or substituted lower alkyl.

A "pharmaceutically acceptable salt" may be any salt derived from an inorganic or organic acid or an inorganic or organic base. The term "pharmaceutically acceptable anion" refers to the anion of such acid addition salts. The term "pharmaceutically acceptable cation" refers to a cation formed by addition of a base. The salt and/or the anion or cation are chosen not to be biologically or otherwise undesirable.

A "therapeutically effective amount" means that amount which, when administered to an animal for treating a disease, is sufficient to effect such treatment for the disease.

"Treating" or "treatment" of a disease in a mammal includes:

(1) preventing the disease from occurring in a mammal which may be predisposed to the disease but does not yet experience or display symptoms of the disease, (2) inhibiting the disease, i.e., arresting its development, or (3) relieving symptoms of the disease, i.e., causing regression of the disease.

The "kinase portion thereof", with respect to the insulin receptor, means the cytoplasmic tyrosine kinase domain of the insulin receptor.

(b) Compounds and Pharmaceutical Compositions Thereof

One aspect of the present invention provides pharmaceutical compositions which comprises (i) a pharmaceutically acceptable carrier and (ii) as an active ingredient, a compound of formula I:

Formula I

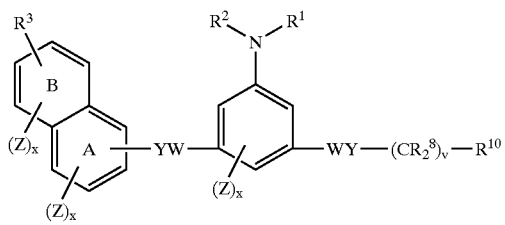

where:

R$^1$ and R$^2$ are, independently, hydrogen, alkyl, substituted alkyl, aryl, substituted aryl, —C(O)R$^4$, —C(O)OR$^4$, —C(O)NR$^4$R$^5$, —S(O)$_2$R$^4$, —S(O)$_2$OR$^4$, heteroaryl, substituted heteroaryl, heterocyclyl substituted heterocyclyl, aryl(lower)alkyl, substituted aryl(lower) alkyl, heteroaryl(lower)alkyl, substituted heteroaryl (lower)alkyl, or lower alkenyl, or R$^1$ and R$^2$ together with the conjoining nitrogen are C$_3$–C$_9$ heteroaryl, C$_3$–C$_5$ heterocyclyl, or both R$^1$ and R$^2$ are oxygen and together with the conjoining nitrogen forming —NO$_2$, R$^3$ is a substituent on the B ring and is —SO$_2$OR$^6$, —C(O)OR$^6$, —SO$_2$NR$^6$$_2$, —C(O)NR$^6$$_2$ or tetrazolyl;

each R$^4$ and R$^5$ is, independently, hydrogen, alkyl, substituted alkyl, aryl, substituted aryl, aryl(lower)alkyl, substituted aryl(lower)alkyl, substituted heteroaryl, heteroaryl, heteroaryl(lower)alkyl, substituted heteroaryl(lower)alkyl, heterocyclyl, substituted heterocyclyl, or lower alkenyl, each R$^6$ and R$^7$ is, independently, hydrogen or lower alkyl, each R$^8$ is, independently, hydrogen, lower alkyl, substituted lower alkyl, aryl(lower)alkyl, substituted aryl (lower)alkyl, substituted heteroaryl, heteroaryl, heteroaryl(lower)alkyl, substituted heteroaryl(lower) alkyl, heterocyclyl, substituted heterocyclyl, lower alkenyl, nitro, halo, cyano, —OR$^9$, —SR$^9$, —C(O)R$^9$, —OC(O)R$^9$, —C(O)OR$^9$, —NR$^9$$_2$, —C(O)NR$^9$$_2$, —NR$^9$C(O)R$^9$, —OSO$_2$R$^9$, —SO$_2$OR$^9$, —SO$_2$NR$^9$$_2$, or —NR$^9$SO$_2$R$^9$, each R$^9$ is, independently, hydrogen, lower alkyl, substituted lower alkyl, aryl, substituted aryl, heteroaryl, substituted heteroaryl, heteroaryl(lower)alkyl, substituted heteroaryl(lower)alkyl, heterocyclyl, substituted heterocyclyl, aryl(lower)alkyl, or substituted aryl (lower)alkyl, R$^{10}$ is aryl, substituted aryl, heteroaryl, or substituted heteroaryl, the linker —WY— between the naphthyl and phenyl intersects the A ring on the naphthyl and is, independently, —C(O)NR$^7$—, —NR$^7$C(O)—, —C(O) O—, —OC(O)—, —CH═CH—, —NR$^7$CH$_2$—, —CH$_2$NR$^7$—, —NR$^7$C(O)NR$^7$—, —NR$^9$C(O)O—, —OC(O)NR$^7$—, —NR$^7$SO$_2$O—, —OSO$_2$NR$^7$—; —OC(O)O—, —SO$_2$NR$^7$—, —NR$^7$SO$_2$—, —OSO$_2$—, or —SO$_2$O—, each Z is a non-interfering substituent, and each x and v is, independently, 0, 1, 2 or 3, as a single stereoisomer or mixture of stereoisomers, or a pharmaceutically acceptable salt thereof.

This pharmaceutical composition is useful for stimulating the uptake of glucose into cells of a mammal or for treating a mammalian disease state such as hyperglycemia, type I diabetes, or type II diabetes.

Another aspect of the invention is directed to a compound of formula I, where: each R$^4$ and R$^5$ is, independently, hydrogen, alkyl, R$^{11}$-substituted alkyl, aryl, R$^{11}$-substituted aryl, aryl(lower)alkyl, R$^{11}$-substituted aryl(lower)alkyl, R$^{11}$-substituted heteroaryl, heteroaryl, heteroaryl(lower)alkyl, substituted R$^{11}$-heteroaryl(lower)alkyl, heterocyclyl, R$^{11}$-substituted heterocyclyl, or lower alkenyl; each R$^{11}$ is, independently, aryl, substituted aryl, alkyl, substituted alkyl, aryl(lower)alkyl, substituted aryl(lower)alkyl, substituted heteroaryl, heteroaryl, heteroaryl(lower)alkyl, substituted heteroaryl(lower)alkyl, heterocyclyl, substituted heterocyclyl, lower alkenyl, nitro, halo, cyano, —OR$^{12}$, —SR$^{12}$, —C(O)R$^{12}$, —OC(O)R$^{12}$; —C(O)OR$^{12}$, —NR$^{12}$$_2$, —C(O)NR$^{13}$$_2$, —NR$^{12}$C(O)R$^3$, —OSO$_2$R$^{12}$, —SO$_2$OR$^{12}$, —SO$_2$NR$^{12}$$_2$, or —NR$^{12}$SO$_2$R$^{12}$; and each R$^{12}$ and R$^{13}$ is, independently, hydrogen, lower alkyl, substituted lower alkyl, aryl, substituted aryl, heteroaryl, substituted heteroaryl, heteroaryl(lower)alkyl, substituted heteroaryl (lower)alkyl, heterocyclyl, substituted heterocyclyl, aryl (lower)alkyl, or substituted aryl(lower)alkyl; with the proviso that if $R^{10}$ is naphthyl, v is 0, and each —WY— is —C(O)NR$^7$— or —NR$^7$C(O)—, then (i) Z is not —SO$_2$OH; and (ii) if $R^1$ or $R^2$ is —C(O)NR$^4$R$^5$, then $R^{13}$ is neither aryl nor substituted aryl.

Preferably, the compounds of formula I are compounds of formula II:

Formula II

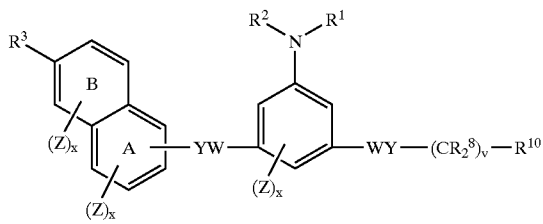

where each $R^1$ through $R^3$, $R^8$, $R^{10}$, —WY—, Z, v, and x are as previously defined for compounds of formula I, as single stereoisomers or mixtures of stereoisomers, or pharmaceutically acceptable salts thereof.

$R^{10}$ of the compounds of formula I–II are preferably aryl or substituted aryl. The aryl or substituted aryl is preferably naphthyl or substituted naphthyl. Alternatively, the aryl or substituted aryl may be phenyl or substituted phenyl. In an alternative preferred embodiment, $R^{10}$ is a heteroaryl or substituted heteroaryl. For instance, $R^{10}$ may be quinolyl.

In a compound of formula I or II, if v is 1, 2, or 3, then, preferably, each $R^8$ is, independently, hydrogen, lower alkyl, substituted lower alkyl, nitro, halo, cyano, —OR$^9$, —SR$^9$, —C(O)R$^9$, —OC(O)R$^9$, —C(O)OR$^9$, —NR$^9{}_2$, —C(O)NR$^9{}_2$, —NR$^9$C(O)R$^9$, —OSO$_2$R$^9$, —SO$_2$OR$^9$, —SO$_2$NR$^9{}_2$, or —NR$^9$SO$_2$R$^9$, where $R^9$ is hydrogen or lower alkyl. In particularly preferred embodiments, $R^8$ is hydrogen, lower alkyl, halo-lower alkyl, nitro, halo, cyano, amino, lower alkyloxy, thio, or —C(O)OR$^9$, where $R^9$ is lower alkyl or hydrogen. In the compounds of formula I and II, v is preferably zero.

Other preferred compounds of formula I are compounds of formula III:

Formula III

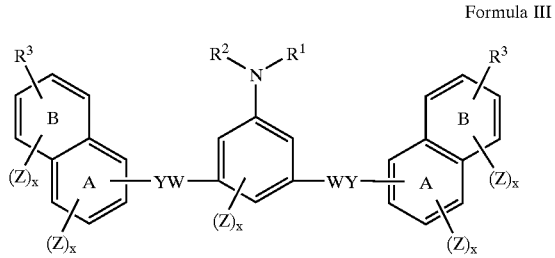

where each substituent $R^1$, $R^2$, $R^3$, —WY—, Z and x is independently defined as in formula I, as single stereoisomers or mixtures of stereoisomers, or pharmaceutically acceptable salts thereof.

Especially preferred compounds of formula III are compounds of formula IV:

Formula IV

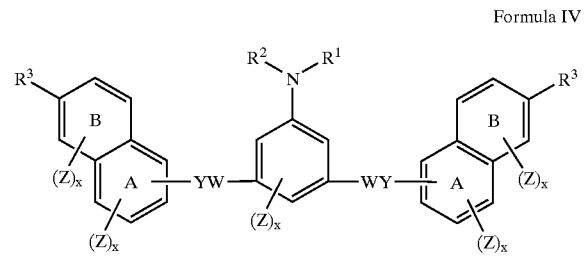

where each substituent $R^1$, $R^2$, $R^3$, —WY—, Z and x is independently defined as for formula I, as single stereoisomers or mixtures of stereoisomers, or pharmaceutically acceptable salts thereof.

Preferably, each non-interfering substituent Z in the compounds of formula I, II, III, and IV is, independently, alkyl, substituted alkyl, cyano, halo, nitro, —SR$^{14}$, —OR$^{14}$, or —NR$^{14}{}_2$, where each $R^{14}$ is, independently, hydrogen, lower alkyl, or substituted lower alkyl. Preferably each Z is lower alkyl, halo-lower alkyl, lower alkyloxy, cyano, halo, thio, amino, nitro, or hydroxy. In preferred compounds of the formulas I–IV, each x is 0 or 1. In the most preferred compounds, each x is 0.

In preferred compounds of formula I, II, III, and IV, $R^1$ is alkyl, substituted alkyl, aryl, substituted aryl, —C(O)R$^4$, —C(O)OR$^4$, —C(O)NR$^4$R$^5$, —S(O)$_2$R$^4$, —S(O)$_2$OR$^4$, heteroaryl, aryl(lower)alkyl, substituted aryl(lower)alkyl; or heteroaryl(lower)alkyl and $R^2$ is hydrogen or lower alkyl. Most preferably, $R^1$ is —C(O)R$^4$, —C(O)NR$^4$R$^5$, or —SO$_2$R$^4$ and $R^2$ is hydrogen or lower alkyl.

In a preferred embodiment of the invention, $R^3$ of the compounds of formula I–IV is —SO$_2$OR$^6$ or —SO$_2$NR$^6{}_2$. In preferred compounds of the invention, $R^3$ is —SO$_2$OH. In an alternative preferred embodiment, $R^3$ is instead —C(O)OR$^6$, —C(O)NR$^6{}_2$ or tetrazolyl. For instance, $R^3$ may be —C(O)OH.

In preferred compounds of formula I–IV, each $R^4$ and $R^5$ is, independently, hydrogen, alkyl, $R^{11}$-substituted alkyl, aryl, $R^{11}$-substituted aryl, aryl(lower)alkyl, $R^{11}$-substituted aryl(lower)alkyl, $R^{11}$-substituted heteroaryl, heteroaryl, heteroaryl(lower)alkyl, substituted $R^{11}$-heteroaryl(lower)alkyl, heterocyclyl, $R^{11}$-substituted heterocyclyl, or lower alkenyl, where each $R^{11}$ is, independently, aryl, substituted aryl, alkyl, substituted alkyl, substituted heteroaryl, heteroaryl, heterocyclyl, substituted heterocyclyl, lower alkenyl, nitro, halo, cyano, —OR$^{12}$, —SR$^{12}$, —C(O)R$^{12}$, —OC(O)R$^{12}$, —C(O)OR$^{12}$, —NR$^{12}{}_2$, —C(O)NR$^{13}{}_2$, —NR$^{12}$C(O)R$^{13}$, —OSO$_2$R$^{12}$, —SO$_2$OR$^{12}$, —SO$_2$NR$^{12}{}_2$, or —NR$^{12}$SO$_2$R$^{12}$ and each $R^{12}$ and $R^{13}$ is, independently, hydrogen, lower alkyl, substituted lower alkyl, aryl, substituted aryl, heteroaryl, substituted heteroaryl, heteroaryl(lower)alkyl, substituted heteroaryl(lower)alkyl, heterocyclyl, substituted heterocyclyl, aryl(lower)alkyl, or substituted aryl(lower)alkyl.

In further preferred compounds of formulas I–IV, $R^4$ is lower alkyl, $R^{11}$-substituted lower alkyl, aryl, $R^{11}$-substituted aryl, aryl(lower)alkyl, $R^{11}$-substituted aryl (lower)alkyl, heteroaryl(lower)alkyl, or heteroaryl and $R^5$ is hydrogen or lower alkyl.

Preferably, each $R^{11}$ is, independently, aryl, $R^{15}$-substituted aryl, lower alkyl, $R^{15}$-substituted lower alkyl, heteroaryl, nitro, halo, cyano, amino, thio, —OR$^{12}$, —C(O)R$^{12}$, —OC(O)R$^{12}$, —C(O)OR$^{12}$, —C(O)NR$^{13}{}_2$, or —NR$^{12}$C(O)R$^{13}$, each $R^{12}$ and $R^{13}$ is, independently, hydrogen, lower alkyl, $R^{15}$-substituted lower alkyl, aryl, $R^{15}$-substituted aryl, heteroaryl, heteroaryl(lower)alkyl, aryl(lower)alkyl, or $R^{15}$-substituted aryl(lower)alkyl, and each $R^{15}$ is, independently, halo, thio, amino, nitro, cyano, hydroxy, lower alkyl, halo-lower alkyl, or lower alkyloxy.

In preferred compounds of formula I, II, III, and IV, each —WY— linker is, independently, —C(O)NR$^7$—, —NR$^7$C(O)—, —SO$_2$NR$^7$—, —NR$^7$SO$_2$—, or —NR$^7$C(O)NR$^7$—. In one embodiment, each —WY— linker is —SO$_2$NR$^7$— or —NR$^7$SO$_2$—. In another embodiment, each —WY— linker is —NR$^7$C(O)NR$^7$—. In one particularly preferred embodiment, each —WY— linker is, independently, —C(O)NR$^7$— or —NR$^7$C(O)—. Compounds of formula I–IV where each —WY— linker is —C(O)NR$^7$— are most preferred.

In compounds of formulas I–IV, each $R^7$ is preferably hydrogen.

Compounds of formula I–IV in which the —WY— linkers are identical are preferred. This is especially true of compounds of formula III and IV. In compounds of formula III and IV, it is also preferred that the $R^3$ substituents be identical to each other and the naphthyl or substituted naphthyl groups to which the $R^3$ radicals are attached also be identical to each other. This symmetry, however, is not required. For instance, in a compound of formula IV, one $R^3$ may be —C(O)OH and the other $R^3$ may be —SO$_2$OH.

Compounds of formula I, II, III, or IV comprising more than one preferred substituent are especially preferred. If a compound comprises more preferred substituents than a second compound, then the first compound is preferred over the second. For instance, compounds of formula IV comprising preferred radicals for the substituents $(Z)_x$, $R^1$, $R^2$, and —WY— are preferred over compounds of formula I comprising preferred radicals for only the substituents (Z), and —WY—.

Examples of preferred compounds of formula I include compounds of formula V:

Formula V

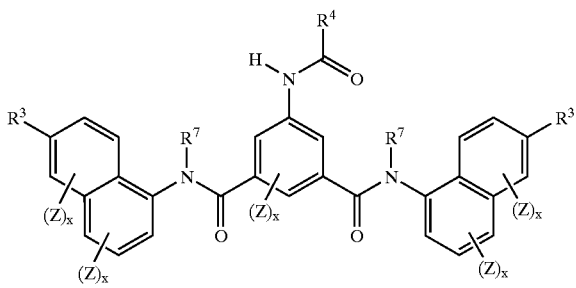

where:

$R^4$ is alkyl, $R^{11}$-substituted alkyl, aryl, $R^{11}$-substituted aryl, aryl(lower)alkyl, $R^{11}$-substituted aryl(lower)alkyl, heteroaryl(lower)alkyl, $R^{11}$-substituted heteroaryl(lower)alkyl, heterocyclyl, $R^{11}$-substituted heterocyclyl, heteroaryl, or $R^{11}$-substituted heteroaryl;

each $R^{11}$ is, independently, aryl, $R^{15}$-substituted aryl, lower alkyl. $R^{15}$-substituted lower alkyl, heteroaryl, nitro, halo, cyano, amino, thio, —OR$^{12}$, —C(O)R$^{12}$, —OC(O)R$^{12}$, —C(O)OR$^{12}$, —C(O)NR$^{13}{}_2$, or —NR$^{12}$C(O)R$^{13}$;

each $R^{12}$ and $R^{13}$ is, independently, hydrogen, lower alkyl, $R^{15}$-substituted lower alkyl, aryl, $R^{15}$-substituted aryl, heteroaryl, heteroaryl(lower)alkyl, aryl(lower)alkyl, or $R^{15}$-substituted aryl(lower)alkyl; and:

$R^{15}$ is, independently, halo, thio, amino, nitro, cyano, hydroxy, lower alkyl or lower alkyloxy;

Z is lower alkyl, halo-lower alkyl, lower alkyloxy, cyano, halo, thio, amino, nitro, or hydroxy; and x is 0, 1, or 2, as single stereoisomers or mixtures of stereoisomers, or pharmaceutically acceptable salts thereof.

A particularly preferred group of compounds are those of formula V, where:

$R^3$ is —SO$_3$H;

$R^4$ is $R^{11}$-substituted phenyl where each $R^{11}$ is independently lower alkyl, $R^{15}$-substituted lower alkyl, lower alkyloxy, cyano, halo, thio, amino, amido, nitro or hydroxy;

$R^7$ is hydrogen; and x is 0.

Other preferred compounds of formula I include compounds of formula VI:

Formula VI

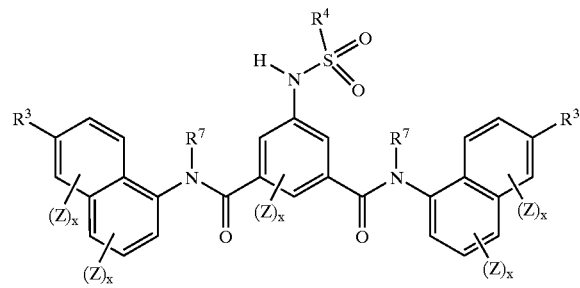

where:

$R^4$ is alkyl, $R^{11}$-substituted alkyl, aryl, $R^{11}$-substituted aryl, aryl(lower)alkyl, $R^{11}$-substituted aryl(lower)alkyl, heteroaryl(lower)alkyl, $R^{11}$-substituted heteroaryl(lower)alkyl, heterocyclyl, $R^{11}$-substituted heterocyclyl, heteroaryl, or $R^{11}$-substituted heteroaryl;

each $R^{11}$ is, independently, aryl, $R^{15}$-substituted aryl, lower alkyl, $R^{15}$-substituted lower alkyl, heteroaryl, nitro, halo, cyano, amino, thio, —OR$^{12}$, —C(O)R$^{12}$, —OC(O)R$^{12}$, —C(O)OR$^{12}$, —C(O)NR$^{13}{}_2$, or —NR$^{12}$C(O)R$^{13}$;

each $R^{12}$ and $R^{13}$ is, independently, hydrogen, lower alkyl, $R^{15}$-substituted lower alkyl, aryl, $R^{15}$-substituted aryl, heteroaryl, heteroaryl(lower)alkyl, aryl(lower)alkyl, or $R^{15}$-substituted aryl(lower)alkyl; and $R^{15}$ is, independently, halo, thio, amino, nitro, cyano, hydroxy, lower alkyl or lower alkyloxy;

Z is lower alkyl, halo-lower alkyl, lower alkyloxy, cyano, halo, thio, amino, nitro, or hydroxy; and x is 0, 1, or 2, as single stereoisomers or mixtures of stereoisomers, or pharmaceutically acceptable salts thereof.

Alternative preferred compounds of formula I include compounds of formula VII:

Formula VII

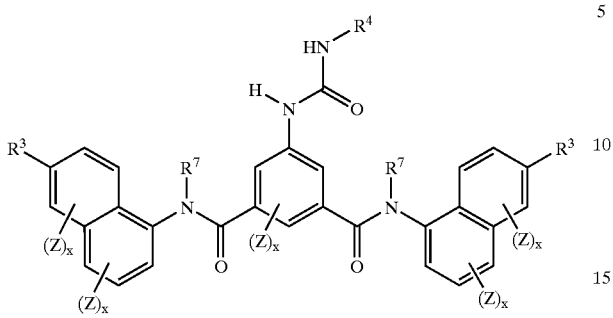

where:
- R⁴ is alkyl, R¹¹-substituted alkyl, aryl, R¹¹-substituted aryl, aryl(lower)alkyl, R¹¹-substituted aryl(lower)alkyl, heteroaryl(lower)alkyl, R¹¹-substituted heteroaryl(lower)alkyl, heterocyclyl, R¹¹-substituted heterocyclyl, heteroaryl, or R¹¹-substituted heteroaryl;
- each R¹¹ is, independently, aryl, R¹⁵-substituted aryl, lower alkyl, R¹⁵-substituted lower alkyl, heteroaryl, nitro, halo, cyano, amino, thio, —OR¹², —C(O)R¹², —OC(O)R¹², —C(O)OR¹², —C(O)NR¹³₂, or —NR¹²C(O)R¹³;
- each R¹² is, independently, hydrogen, lower alkyl, R¹⁵-substituted lower alkyl, aryl, R¹⁵-substituted aryl, heteroaryl, heteroaryl(lower)alkyl, aryl(lower)alkyl, or R¹⁵-substituted aryl(lower)alkyl;
- each R¹³ is, independently, hydrogen, lower alkyl, R¹⁵-substituted lower alkyl, heteroaryl, heteroaryl(lower)alkyl, aryl(lower)alkyl, or R¹⁵-substituted aryl(lower)alkyl;
- R¹⁵ is, independently, halo, thio, amino, nitro, cyano, hydroxy, lower alkyl or lower alkyloxy;
- Z is lower alkyl, halo-lower alkyl, lower alkyloxy, cyano, halo, thio, amino, nitro, or hydroxy; and
- x is 0, 1, or 2, as single stereoisomers or mixtures of stereoisomers, or pharmaceutically acceptable salts thereof.

Additional preferred compounds of formula I are represented by formula VIII:

Formula VIII

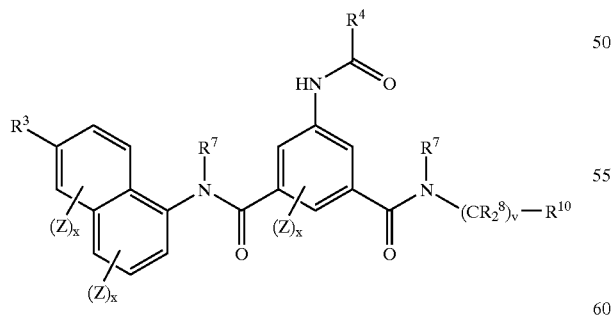

where:
- R⁴ is alkyl, R¹¹-substituted alkyl, aryl, R¹¹-substituted aryl, aryl(lower)alkyl, R¹¹-substituted aryl(lower)alkyl, heteroaryl(lower)alkyl, R¹¹-substituted heteroaryl(lower)alkyl, heterocyclyl, R¹¹-substituted heterocyclyl, heteroaryl, or R¹¹-substituted heteroaryl;
- each R⁸ is, independently, hydrogen, lower alkyl, substituted lower alkyl, nitro, halo, cyano, —OR⁹, —SR⁹, —C(O)R⁹, —OC(O)R⁹, —C(O)OR⁹, —NR⁹₂, —C(O)NR⁹₂, —NR⁹C(O)R⁹, —OSO₂R⁹, —SO₂OR⁹, —SO₂NR⁹₂, or —NR⁹SO₂R⁹; and
- each R⁹ is, independently, hydrogen or lower alkyl;
- R¹⁰ is aryl, R¹⁵-substituted aryl, heteroaryl, or R¹⁵-substituted heteroaryl;
- each R¹¹ is, independently, aryl, R¹⁵-substituted aryl, lower alkyl, R¹⁵-substituted lower alkyl, heteroaryl, nitro, halo, cyano, amino, thio, —OR¹², —C(O)R¹², —OC(O)R¹², —C(O)OR¹², —C(O)NR¹³₂, or —NR¹²C(O)R¹³;
- each R¹² and R¹³ is, independently, hydrogen, lower alkyl, R¹⁵-substituted lower alkyl, aryl, R¹⁵-substituted aryl, heteroaryl, heteroaryl(lower)alkyl, aryl(lower)alkyl, or R¹⁵-substituted aryl(lower)alkyl; and
- R¹⁵ is, independently, halo, thio, amino, nitro, cyano, hydroxy, lower alkyl or lower alkyloxy;
- Z is lower alkyl, halo-lower alkyl, lower alkyloxy, cyano, halo, thio, amino, nitro, or hydroxy; and
- each x is, independently, 0, 1, or 2, as single stereoisomers or mixtures of stereoisomers, or pharmaceutically acceptable salts thereof.

Compounds of the formulas V–VIII are particularly preferred when each R³ is —SO₃H or tetrazolyl and each R⁷ is hydrogen. Alternatively, each R³ is —COOH and each R⁷ is hydrogen.

Compounds of the present invention which are suitable for use in pharmaceutical compositions and methods of the invention, include, but are not limited to the following compounds:

- 5-({3-[(3-methylphenyl)carbonylamino]-5-[N-(6-sulfonaphthyl)carbamoyl]phenyl}carbonylamino) naphthalene-2-sulfonic acid;
- 5-({3-[(4-methylphenyl)carbonylamino]-5-[N-(6-sulfonaphthyl)carbamoyl]phenyl}carbonylamino) naphthalene-2-sulfonic acid;
- 5-({3-[(4-methoxyphenyl)carbonylamino]-5-[N-(6-sulfonaphthyl)carbamoyl]phenyl}carbonylamino) naphthalene-2-sulfonic acid;
- 5-({3-[(3-chlorophenyl)carbonylamino]-5-[N-(6-sulfonaphthyl)carbamoyl]phenyl}carbonylamino) naphthalene-2-sulfonic acid;
- 5-({3-[(3-fluorophenyl)carbonylamino]-5-[N-(6-sulfonaphthyl)carbamoyl]phenyl}carbonylamino) naphthalene-2-sulfonic acid;
- 5-({3-[(4-fluorophenyl)carbonylamino]-5-[N-(6-sulfonaphthyl)carbamoyl]phenyl}carbonylamino) naphthalene-2-sulfonic acid;
- 5-({3-[(3-methoxyphenyl)carbonylamino]-5-[N-(6-sulfonaphthyl)carbamoyl]phenyl}carbonylamino) naphthalene-2-sulfonic acid;
- 5-({3-[(4-nitrophenyl)carbonylamino]-5-[N-(6-sulfonaphthyl)carbamoyl]phenyl}carbonylamino) naphthalene-2-sulfonic acid;
- 5-({3-[(3-nitrophenyl)carbonylamino]-5-[N-(6-sulfonaphthyl)carbamoyl]phenyl}carbonylamino) naphthalene-2-sulfonic acid;
- 5-({3-[(3-nitro-4-methylphenyl)carbonylamino]-5-[N-(6-sulfonaphthyl)carbamoyl]phenyl}carbonylamino) naphthalene-2-sulfonic acid;
- 2-(N-{3,5-bis[N-(6-sulfonaphthyl)carbamoyl]phenyl}carbamoyl)benzoic acid;

2-(N-{3,5-bis[N-(6-sulfonaphthyl)carbamoyl]
phenyl}carbamoyl)-4,5-dichlorobenzoic acid;

5-({3-[(4-chlorophenyl)carbonylamino]-5-[N-(6-
sulfonaphthyl)carbamoyl]phenyl}carbonylamino)
naphthalene-2-sulfonic acid;

2-(N-{3,5-bis[N-(6-sulfonaphthyl)carbamoyl]
phenyl}carbamoyl)-3,5-dichlorobenzoic acid;

2-(N-{3,5-bis[N-(6-sulfonaphthyl)carbamoyl]
phenyl}carbamoyl)-6-hydroxybenzoic acid;

5-({3-(phenylcarbonylamino)-5-[N-(6-sulfonaphthyl)
carbamoyl]phenyl}carbonylamino)naphthalene-2-
sulfonic acid;

5-({3-(acetylamino)-5-[N-(6-sulfonaphthyl)carbamoyl]
phenyl}carbonylamino)naphthalene-2-sulfonic acid;

5-({3-(2-naphthylcarbonylamino)-5-[N-(6-
sulfonaphthyl)carbamoyl]phenyl}carbonylamino)
naphthalene-2-sulfonic acid;

5-({3-(1-naphthylcarbonylamino)-5-[N-(6-
sulfonaphthyl)carbamoyl]phenyl}carbonylamino)
naphthalene-2-sulfonic acid;

5-({3-[(2-methylphenyl)carbonylamino]-5-[N-(6-
sulfonaphthyl)carbamoyl]phenyl}carbonylamino)
naphthalene-2-sulfonic acid;

(3S)-3-amino-3-(N-{3,5-bis[N-(6-sulfonaphthyl)
carbamoyl]phenyl}carbamoyl)propanoic acid;

3-(N-{3,5-bis[N-(6-sulfonaphthyl)carbamoyl]
phenyl}carbamoyl)-3-phenylpropanoic acid;

3-(N-{3,5-bis[N-(6-sulfonaphthyl)carbamoyl]
phenyl}carbamoyl)-2-phenylpropanoic acid;

5-({5-[N-(6-sulfonaphthyl)carbamoyl]-3-[(2-
sulfophenyl)carbonylamino]phenyl}carbonylamino)
naphthalene-2-sulfonic acid;

3-(N-{3,5-bis[N-(6-sulfonaphthyl)carbamoyl]
phenyl}carbamoyl)benzoic acid;

4-(N-{3,5-bis[N-(6-sulfonaphthyl)carbamoyl]
phenyl}carbamoyl)benzoic acid;

3-(N-{3,5-bis[N-(6-sulfonaphthyl)carbamoyl]
phenyl}carbamoyl)propanoic acid;

5-({3-(cyclohexylcarbonylamino)-5-[N-(6-
sulfonaphthyl)carbamoyl]phenyl}carbonylamino)
naphthalene-2-sulfonic acid;

5-({3-(2-furylcarbonylamino)-5-[N-(6-sulfonaphthyl)
carbamoyl]phenyl}carbonylamino)naphthalene-2-
sulfonic acid;

5-({3-(4-pyridylcarbonylamino)-5-[N-(6-sulfonaphthyl)
carbamoyl]phenyl}carbonylamino)naphthalene-2-
sulfonic acid;

5-({3-(3-pyridylcarbonylamino)-5-[N-(6-sulfonaphthyl)
carbamoyl]phenyl}carbonylamino)naphthalene-2-
sulfonic acid;

5-({3-(2-phenylacetylamino)-5-[N-(6-sulfonaphthyl)
carbamoyl]phenyl}carbonylamino)naphthalene-2-
sulfonic acid 5-({3-(2-phenoxyacetylamino)-5-[N-(6-sulfonaphthyl)
carbamoyl]phenyl}carbonylamino)naphthalene-2-
sulfonic acid;

5-({3-(2-oxo-2-(2-quinolyl)acetylamino)-5-[N-(6-
sulfonaphthyl)carbamoyl]phenyl}carbonylamino)
naphthalene-2-sulfonic acid;

5-({3-[2-(4-methylphenoxy)acetylamino]-5-[N-(6-
sulfonaphthyl)carbamoyl]phenyl}carbonylamino)
naphthalene-2-sulfonic acid;

5-({3-[2-(4-methoxyphenyl)acetylamino]-5-[N-(6-
sulfonaphthyl)carbamoyl]phenyl}carbonylamino)
naphthalene-2-sulfonic acid;

5-[(3-{3-[N-(4-methylphenyl)carbamoyl]
propanoylamino}-5-[N-(6-sulfonaphthyl)carbamoyl]
phenyl)carbonylamino]naphthalene-2-sulfonic acid;

5-({3-[2-(4-methylphenyl)acetylamino]-5-[N-(6-
sulfonaphthyl)carbamoyl]phenyl}carbonylamino)
naphthalene-2-sulfonic acid;

5-({3-[2-(3-chlorophenyl)acetylamino]-5-[N-(6-
sulfonaphthyl)carbamoyl]phenyl}carbonylamino)
naphthalene-2-sulfonic acid;

5-({5-[(3-amino-4-methylphenyl)carbonylamino]-3-[N-
(6-sulfonaphthyl)carbamoyl]phenyl}carbonylamino)
naphthalene-2-sulfonic acid;

5-({5-(2-(2-naphthyloxy)acetylamino)-3-[N-(6-
sulfonaphthyl)carbamoyl]phenyl}carbonylamino)
naphthalene-2-sulfonic acid;

5-({5-[(7-methoxybenzo[d]furan-2-yl)carbonylamino]-3-
[N-(6-sulfonaphthyl)carbamoyl]
phenyl}carbonylamino)naphthalene-2-sulfonic acid;

5-({3-[(phenylsulfonyl)amino]-5-[N-(6-sulfonaphthyl)
carbamoyl]phenyl}carbonylamino)naphthalene-2-
sulfonic acid;

5-({3-[(2-naphthylsulfonyl)amino]-5-[N-(6-
sulfonaphthyl)carbamoyl]phenyl}carbonylamino)
naphthalene-2-sulfonic acid;

5-[(3-{[(4-chlorophenyl)sulfonyl]amino}-5-[N-(6-
sulfonaphthyl)carbamoyl]phenyl)carbonylamino]
naphthalene-2-sulfonic acid;

5-[(3-{[(4-fluorophenyl)sulfonyl]amino}-5-[N-(6-
sulfonaphthyl)carbamoyl]phenyl)carbonylamino]
naphthalene-2-sulfonic acid;

5-[(3-{[(4-methoxyphenyl)sulfonyl]amino}-5-[N-(6-
sulfonaphthyl)carbamoyl]phenyl)carbonylamino]
naphthalene-2-sulfonic acid;

5-[(3-{[(4-methylphenyl)sulfonyl]amino}-5-[N-(6-
sulfonaphthyl)carbamoyl]phenyl)carbonylamino]
naphthalene-2-sulfonic acid;

5-({3-[(1-naphthylsulfonyl)amino]-5-[N-(6-
sulfonaphthyl)carbamoyl]phenyl}carbonylamino)
naphthalene-2-sulfonic acid;

5-[(3-{[(2,4,6-trimethylphenyl)sulfonyl]amino}5-[N-(6-
sulfonaphthyl)carbamoyl]phenyl)carbonylamino]
naphthalene-2-sulfonic acid;

5-[(5-{[benzylsulfonyl]amino}-3-[N-(6-sulfonaphthyl)
carbamoyl]phenyl)carbonylamino]naphthalene-2-
sulfonic acid;

5-[(3-{[(3-chlorophenyl)amino]carbonylamino}-5-[N-(6-
sulfonaphthyl)carbamoyl]phenyl)carbonylamino]
naphthalene-2-sulfonic acid;

5-[(3-{[(4-chlorophenyl)amino]carbonylamino}-5-[N-(6-
sulfonaphthyl)carbamoyl]phenyl)carbonylamino]
naphthalene-2-sulfonic acid;

5-[(3-{[(2-chlorophenyl)amino]carbonylamino}-5-[N-(6-
sulfonaphthyl)carbamoyl]phenyl)carbonylamino]
naphthalene-2-sulfonic acid;

5-[(3-{[(2-methylphenyl)amino]carbonylamino}-5-[N-
(6-sulfonaphthyl)carbamoyl]phenyl)carbonylamino]
naphthalene-2-sulfonic acid;

5-[(3-{[(3-methylphenyl)amino]carbonylamino}-5-[N-
(6-sulfonaphthyl)carbamoyl]phenyl)carbonylamino]
naphthalene-2-sulfonic acid;

5-[(3-{[(4-methylphenyl)amino]carbonylamino}-5-[N-
(6-sulfonaphthyl)carbamoyl]phenyl)carbonylamino]
naphthalene-2-sulfonic acid;

5-[(3-{[(2-methoxyphenyl)amino]carbonylamino}-5-[N-(6-sulfonaphthyl)carbamoyl]phenyl)carbonylamino]naphthalene-2-sulfonic acid;

5-[(3-{[(3-methoxyphenyl)amino]carbonylamino}-5-[N-(6-sulfonaphthyl)carbamoyl]phenyl)carbonylamino]naphthalene-2-sulfonic acid;

5-[(3-{[(4-methoxyphenyl)amino]carbonylamino}-5-[N-(6-sulfonaphthyl)carbamoyl]phenyl)carbonylamino]naphthalene-2-sulfonic acid;

5-({3-[(phenylamino)carbonylamino]-5-[N-(6-sulfonaphthyl)carbamoyl]phenyl}carbonylamino)naphthalene-2-sulfonic acid;

5-({3-[(3-chlorophenyl)carbonylamino]-5-[N-(6-hydroxynaphthyl)carbamoyl]phenyl}carbonylamino)naphthalene-2-sulfonic acid;

5-({3-[(3-Chlorophenyl)carbonylamino]-5-(N-naphthylcarbamoyl)phenyl}carbonylamino)naphthalene-2-sulfonic acid;

5-({3-[(4-methylphenyl)carbonylamino]-5-(N-(8-quinolyl)carbamoyl)phenyl}carbonylamino)naphthalene-2-sulfonic acid;

(2S)-2-({5-[(4-methylphenyl)carbonylamino]-3-[N-(6-sulfonaphthyl)carbamoyl]phenyl}carbonylamino)-3-phenylpropanoic acid;

5-({3-[(4-methylphenyl)carbonylamino]-5-[N-(6-sulfamoylnaphthyl)carbamoyl]phenyl}carbonylamino)naphthalene-2-sulfonic acid;

5-({5-[N-(6-carboxynaphthyl)carbamoyl]-3-[(4-methylphenyl)carbonylamino]-phenyl}carbonylamino)naphthalene-2-carboxylic acid;

5-({3-amino-5-[N-methyl-N-(6-sulfonaphthyl)carbamoyl]phenyl}-N-methylcarbonylamino)naphthalene-2-sulfonic acid; and 5-({5-[(3-chlorophenyl)carbonylamino]-3-[N-methyl-N-(6-sulfonaphthyl)carbamoyl]phenyl}-N-methylcarbonylamino)-naphthalene-2-sulfonic acid;

as single stereoisomers or mixtures of stereoisomers, and the pharmaceutically acceptable salts thereof.

Syntheses and descriptions of these compounds are outlined in Examples 1 through 11.

Certain compounds of the invention may contain one or more chiral centers. In such cases, all stereoisomers also fall within the scope of this invention. The invention compounds include the individually isolated stereoisomers as well as mixtures of such stereoisomers.

Pharmaceutically acceptable salts, cations and anions of the compounds of the invention are also encompassed by the present invention and are useful in the methods and pharmaceutical compositions described herein.

Pharmaceutically acceptable salts include salts which may be formed when acidic protons present are capable of reacting with inorganic or organic bases. Typically the parent compound is treated with an excess of an alkaline reagent, such as hydroxide, carbonate or alkoxide, containing an appropriate cation. Cations such as $Na^+$, $K^+$, $Ca^{2+}$ and $NH_4^+$ are examples of cations present in pharmaceutically acceptable salts. The $Na^+$ salts are especially useful. Acceptable inorganic bases, therefore, include aluminum hydroxide, calcium hydroxide, potassium hydroxide, sodium carbonate and sodium hydroxide. Salts may also be prepared using organic bases, such as salts of primary, secondary and tertiary amines, substituted amines including naturally-occurring substituted amines, and cyclic amines including isopropylamine, trimethylamine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, N-ethylpiperidine, and the like.

If the compounds of the invention contain a basic group, an acid addition salt may be prepared. Acid addition salts of the compounds are prepared in a standard manner in a suitable solvent from the parent compound and an excess of acid, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluenesulfonic acid, hexanoic acid, heptanoic acid, cyclopentanepropionic acid, lactic acid, o-(4-hydroxy-benzoyl)benzoic acid, 1,2-ethanedisulfonic acid, 2-hydroxyethanesulfonic acid, benzenesulfonic acid, p-chlorobenzenesulfonic acid, 2-naphthalenesulfonic acid, camphorsulfonic acid, 4-methyl-bicyclo[2.2.2.]oct-2-ene-1-carboxylic acid, glucoheptonic acid, gluconic acid, 4,4'-methylenebis(3-hydroxy-2-naphthoic)acid, 3-phenylpropionic acid, trimethylacetic acid, t-butylacetic acid, laurylsulfuric acid, glucuronic acid, glutamic acid, 3-hydroxy-2-naphthoic acid, stearic acid, muconic acid and the like.

Certain of the compounds form inner salts or zwitterions.

The pharmaceutical compositions of the invention preferably comprise a preferred compound of formula I. For instance, the pharmaceutical composition may comprise a compound of formula II, III, IV, V, VI, VII, or VIII as an active ingredient. However, pharmaceutical compositions which comprise any of the compounds of the invention are contemplated. In all cases, the pharmaceutical compositions of the invention also comprise a pharmaceutically acceptable carrier.

The pharmaceutical compositions of this invention may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, 5% dextrose in water or buffered sodium or ammonium acetate solution. Such formulations are especially suitable for parenteral administration, but may also be used for oral administration. It may be desirable to add excipients such as polyvinylpyrrolidinone, gelatin, hydroxycellulose, acacia, polyethylene glycol, mannitol, sodium chloride or sodium citrate. Alternatively, these compounds may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulation, and compressing, when necessary, for tablet forms; or milling, mixing and filling for hard gelatin capsule forms. When a liquid carrier is use, the preparation will be in the form of a syrup, elixir, emulsion or an aqueous or non-aqueous suspension. Such a liquid formulation may be administered directly p.o. or filled into a soft gelatin capsule.

Some specific examples of suitable pharmaceutical compositions are described in Examples 15–17, below.

Typically, a pharmaceutical composition of the present invention would be packaged in a container with a label indicating use of the pharmaceutical composition in the treatment of hyperglycemia, type I diabetes, or type II diabetes, or a combination of the disease conditions.

(c) Methods of Use of Compounds of this Invention

Figure 2:
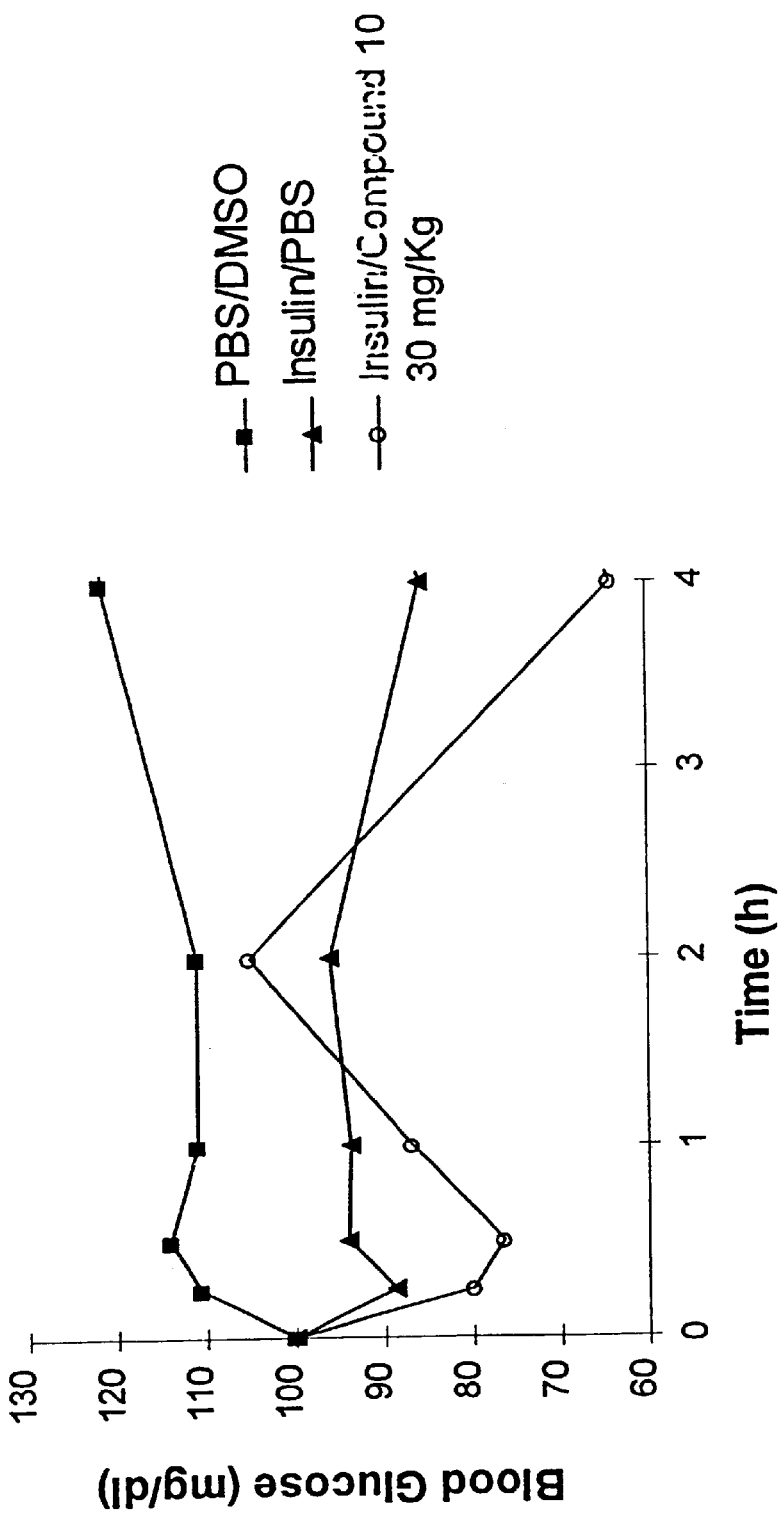
FIG. 2 shows the effect of another compound of the invention, compound 10, in combination with insulin on blood glucose levels in db/db mice.

Compounds of the invention have been found to bind to the kinase domain and stimulate autophosphorylation of the receptor (Example 12, below). In addition, these compounds have been shown to enhance insulin's ability to effect the transport of glucose into cultured fibroblast cells (Example 13, below). The compounds have also been shown to lower blood glucose levels in db/db mice (FIGS. 1 and 2, Example 14).

The ability of compounds of the invention to stimulate autophosphorylation of the insulin receptor and to stimulate the uptake of glucose into cells which is demonstrated in the specific examples, Example 12–14, below, indicates their usefulness in the treatment and management of subjects with diabetes. Without intending to be bound by any theory, it is believed that the compounds of this invention act directly on the kinase function of the receptor and do not necessarily compete with insulin for binding at the insulin-binding site, nor do they effect activation of the receptor by a mechanism similar to that exhibited by insulin. Thus, they are directly able to activate the kinase to autophosphorylate, to potentiate the effect of insulin, to activate the kinase function of the receptor in phosphorylating exogenous substrates and to effect the increased uptake of glucose by adipocytes and insulin receptor-bearing cells in general and to lower blood glucose in diabetic subjects. Accordingly, by virtue of the activities of the compounds of the invention, they may be used to stimulate the kinase activity of an insulin receptor, to enhance the activation of the insulin receptor by insulin, to enhance the stimulation by insulin of cellular glucose uptake, and to stimulate the uptake of glucose in diabetic subjects. Thus, the compounds of this invention are useful in the treatment of diabetes.

One aspect of the invention is directed to a method of stimulating the kinase activity of the insulin receptor. This method comprises contacting the insulin receptor, or the kinase portion thereof, with a compound of the invention in an amount sufficient to stimulate the kinase activity of the insulin receptor. By stimulating the kinase activity of the insulin receptor, both autophosphorylation as well as the phosphorylation of exogenous substrates is enhanced. The stimulation of the kinase activity of the insulin receptor may occur either in vivo or in vitro.

In another aspect of the invention, the insulin receptor is activated by contacting the insulin receptor, or the kinase portion thereof, with a compound of the invention in an amount sufficient to stimulate insulin's activation of the its receptor, optionally in the presence of insulin. The targeted insulin receptor may optionally be on the surface of a cell in a mammal. In such a case, the contacting is effected by administering the compound, or a pharmaceutical composition thereof, to the mammal.

In still another aspect: of the invention, the compounds of the invention are used to stimulate the uptake of glucose into cells displaying the insulin receptor. This method comprises contacting the cells with a compound of the invention, optionally in the presence of insulin, and in an amount sufficient to stimulate the uptake of glucose into the cells. The targeted cells may optionally be in a mammal and the step of contacting the receptor with the compound may then be effected by administering the compound, or pharmaceutical composition thereof, to the mammal.

A method of treating hyperglycemia in a mammal, preferably a human, is provided by another aspect of the invention. The method of treating hyperglycemia in a mammal comprises administering a therapeutically effective amount of a compound of the invention, or a pharmaceutical composition thereof, to the mammal. Optionally, the method may further comprise treating the mammal with an additional form of therapy for hyperglycemia. For instance, one method may also comprise administering to the mammal with insulin in addition to the compounds of the invention. Alternatively, the compounds of the invention may be administered to the mammal in combination with a non-insulin drug or other alternative treatment for hyperglycemia. The total amount of the combination of drugs administered to the mammal must be a therapeutically effective amount, although the amounts of each of the individual drugs may be themselves be suboptimal for therapeutic purposes.

A very dangerous side-effect of the administration of insulin is insulin-induced hypoglycemia with the potential for coma and, possibly, death. This problem can become quite severe in diabetic patients who develop unpredictable responses to insulin or have hyper-variable levels of circulating glucose. For these patients, the co-administration of the compounds of the invention with sub-therapeutic doses of insulin will minimize the possibility that the diabetic patient will over-dose on insulin and suffer from the severe consequences such as coma and death. These compounds appear to be incapable of inducing hypoglycemia in the presence of insulin. They appear to increase the effectiveness of insulin but do not display true insulin mimetic effects like hypoglycemia. These compounds are, thus, effective insulin safeners.

Still another aspect of the invention relates to a method of treating type I diabetes in a mammal. This method comprises administering a therapeutically effective amount of a compound of the invention, or a pharmaceutical composition thereof, to the mammal. In a preferred embodiment, the mammal is a human. The method may optionally further comprise treating the mammal with an additional form of therapy for type I diabetes. For instance, insulin may also be administered to the mammal. The amount of insulin which is delivered to the mammal should be in a therapeutically effective amount when used in conjunction with a compound of the invention. However, the amount delivered to a mammal in conjunction with a compound of the invention is preferably less than an amount which would be therapeutically effective if delivered to the mammal alone. It is understood that the insulin which is administered in any of the treatments of the present invention may either be isolated from a natural source or recombinant. In addition, an insulin analog may be substituted for insulin in any of the treatments of the present invention.

In still further aspects of the invention, the compounds of the invention, or pharmaceutical compositions thereof, are used to treat type II diabetes in a mammal. This method comprises administering a therapeutically effective amount of a compound of the invention, or a pharmaceutical composition thereof, to the mammal. Again, the preferred subject is a human. Again, like the other treatment methods of the invention, this method may further comprise treating the mammal with an additional form of therapy for type II diabetes, such as administering insulin to the mammal.

The compounds of the invention, or pharmaceutical compositions thereof, are thus used to enhance glucose uptake in patients which require such treatment. The method of treatment comprises the administration parenterally, and orally, of an effective quantity of the chosen compound, preferably dispersed in a pharmaceutical carrier. The effective doses of the compound of the invention are generally selected from the range of 0.01 to 1000 mg/kg, preferably 0.01 to 100 mg/kg and more preferably 1–30 mg/kg, but will be readily determined by one skilled in the art depending upon the route of administration, age and condition of the patient. The dosage units may be administered one to ten times daily for acute or chronic disease. No unacceptable toxicological effects are expected when compounds of the invention are administered in accordance with the present invention.

The compounds of formula the invention, or pharmaceutical compositions thereof, may be administered by any route suitable to the subject being treated and the nature of the subject's condition. Routes of administration include, but are not limited to, administration by injection, including intravenous, intraperitoneal, intramuscular, and subcutaneous injection, by transmucosal or transdermal delivery, through topical applications, nasal spray, suppository and the like or may be administered orally. Formulations may optionally be liposomal formulations, emulsions, formulations designed to administer the drug across mucosal membranes or transdermal formulations. Suitable formulations for each of these methods of administration may be found, for example, in *Remington's Pharmaceutical Sciences*, latest edition, Mack Publishing Company, Easton, Pa.

The compounds of the invention have been demonstrated to exhibit stimulatory activity at the insulin receptor with subsequent lowering of circulating glucose levels for a potential therapeutic effect in diabetes illness. Similarly, other compounds which show the same effects on the insulin receptor and, thus, on circulating glucose have the potential to be useful for the treatment of diabetes diseases. The compounds claimed within this patent can be used as a model to discover other new agents that act on the insulin receptor and thereby lower circulating levels of glucose in diabetic patients. The steps in a process in which these agents can be utilized to discover new insulin receptor agonists/activators and glucose-lowering therapeutic agents may be achieved by the following. The compounds may be utilized to validate, optimize, and standardize assays necessary for the discovery of other compounds that:

1. Activate/stimulate the cytoplasmic kinase domain of the insulin receptor kinase or the insulin receptor kinase;
2. Activate/stimulate the insulin receptor;
3. Stimulate glucose uptake into cells and tissues;
4. Lower circulating glucose levels in mammals;
5. Lower circulating glucose levels in humans;
6. Inhibit lipolysis in cells and tissues;
7. Inhibit lipolysis in mammals.

These compounds can be utilized as a benchmark to discover compounds that show improved activity in assays that:

1. Activate/stimulate the cytoplasmic kinase domain of the insulin receptor kinase or the insulin receptor kinase;
2. Activate/stimulate the insulin receptor;
3. Stimulate glucose uptake into cells and tissues;
4. Lower circulating glucose levels in mammals;
5. Lower circulating glucose levels in humans;
6. Inhibit lipolysis in cells and tissues;
7. Inhibit lipolysis in mammals.

Combined with algorithms that compare structures or chemical properties and/or match structures or chemical properties within libraries of test compounds, these compounds can be utilized to discover compounds that display activity in bioassays that:

1. Activate/stimulate the cytoplasmic kinase domain of the insulin receptor kinase or the insulin receptor kinase;
2. Activate/stimulate the insulin receptor;
3. Stimulate glucose uptake into cells and tissues;
4. Lower circulating glucose levels in mammals;
5. Lower circulating glucose levels in humans;
6. Inhibit lipolysis in cells and tissues;
7. Inhibit lipolysis in mammals.

Combined with algorithms that compare structures and/or match structures for the purpose of modeling molecular interactions, these compounds can be utilized to discover compounds that display activity in bioassays that:

1. Activate/stimulate the cytoplasmic kinase domain of the insulin receptor kinase or the insulin receptor kinase;
2. Activate/stimulate the insulin receptor;
3. Stimulate glucose uptake into cells and tissues;
4. Lower circulating glucose levels in mammals;
5. Lower circulating glucose levels in humans;
6. Inhibit lipolysis in cells and tissues;
7. Inhibit lipolysis in mammals.

(d) Examples

The Examples which follow serve to illustrate this invention. The Examples are intended to in no way limit the scope of this invention, but are provided to show how to make and use compounds of the invention.

The compounds of the invention are prepared by conventional methods of organic chemistry. In some cases, protective groups may be introduced and later removed. Suitable protective groups for amino, hydroxyl, carboxyl groups are described in Greene, et al., *Protective Groups in Organic Synthesis*, Second Edition, John Wiley and Sons, New York, 1991. Activation of carboxylic acids can be achieved by using a number of different reagents as described in Larock, *Comprehensive Organic Transformations*, VCH Publishers, New York, 1989.

The compounds of the invention can be synthesized as shown in the following examples or by modifying the exemplified syntheses by means known to those of ordinary skill in the art.

Example 1

Synthesis of 5-({3-[(3-Methylphenyl)carbonylamino]-5-[N-(6-sulfonaphthyl)-carbamoyl]phenyl}carbonylamino)naphthalene-2-sulfonic Acid (Compound 7)

One synthetic route according to the present invention is outlined in Reaction Scheme I, below:

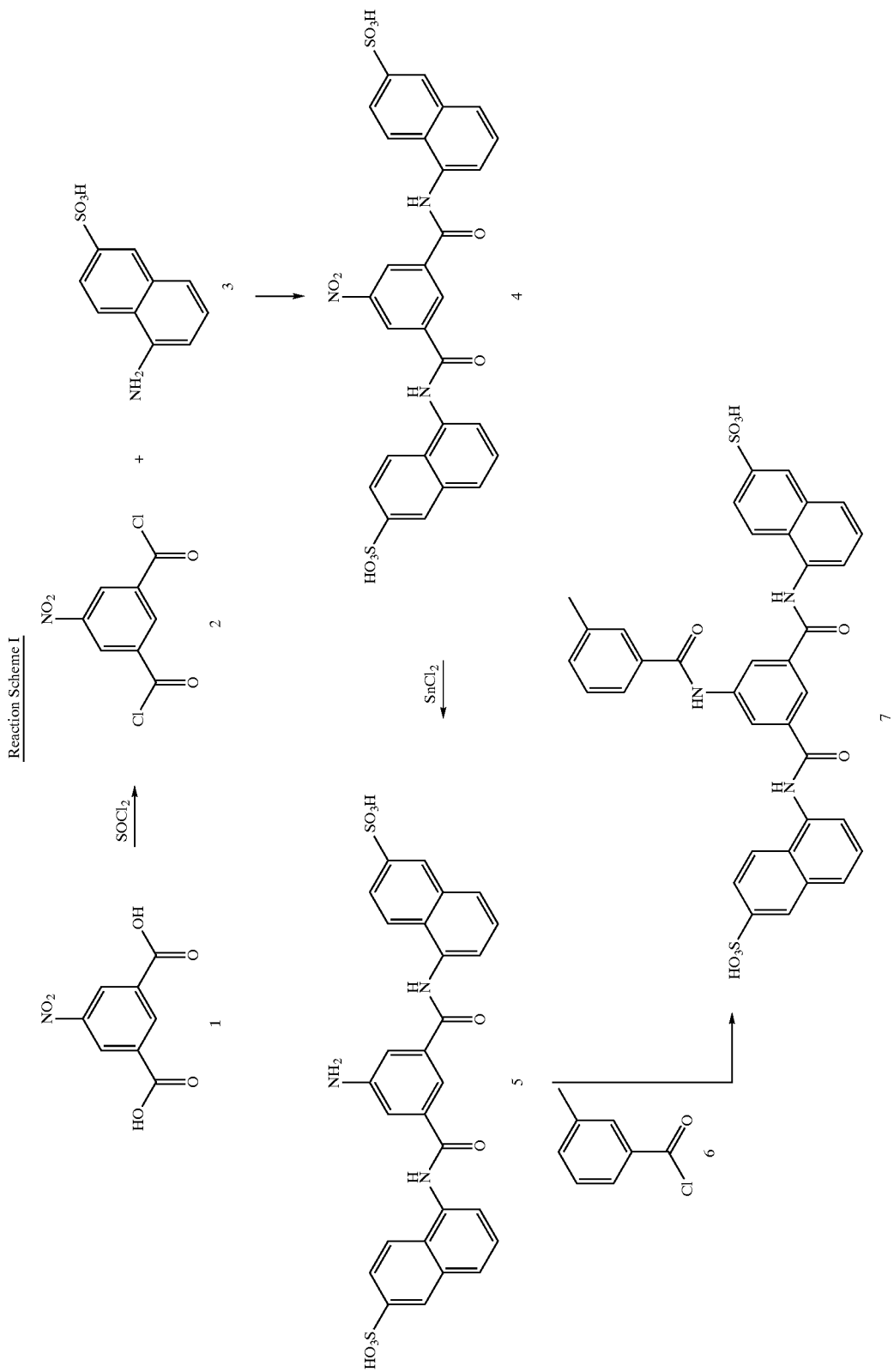

5-Nitrobenzene-1,3-dicarboxylic acid, compound 1, was converted to the di-acid chloride (5-nitrobenzene-1,3-dicarbonyl chloride, compound 2) by the action of an excess of thionyl chloride in pyridine. The di-acid chloride was next reacted with 2 equivalents of 5-amino-2-naphthalene sulfonic acid, compound 3, to give the bis-amide (5-({3-nitro-5-[N-(6-sulfonaphthyl)carbamoyl]phenyl}-carbonylamino)-naphthalene-2-sulfonic acid, compound 4). The nitro group of compound 4 was reduced using tin(II) chloride in aqueous acid solution to give 5-({3-amino-5-[N-(6-sulfonaphthyl)carbamoyl]phenyl}carbonylamino)naphthalene-2-sulfonic acid, compound 5. Compound 5 was reacted with 3-methylbenzoyl chloride, compound 6, to furnish compound 7.

Preparation of 5-({3-Nitro-5-[N-(6-sulfonaphthyl)carbamoyl]phenyl}carbonylamino)-naphthalene-2-sulfonic Acid (Compound 4)

10.56 g (0.05 mole) of 5-nitrobenzene-1,3-dicarboxylic acid was suspended in 12 mL (0.165 mol) of thionyl chloride and then added to 5–7 mL pyridine. The mixture was stirred at room temperature until it became a clear solution and then stirred for one more hour. The excess of thionyl chloride was removed under vacuum.

22.33 g (0.10 mol) of 5-amino-2-naphthalenesulfonic acid was suspended in 150 mL of pyridine and added to the above di-acid chloride in 50 mL (50:50) of dioxane and $CHCl_3$ under vigorous stirring for 1–2 hrs. The crude product was precipitated with dioxane. The oily product was collected on a Büchner funnel. The brown colored oily product was dissolved in 500 mL water, then allowed to precipitate out over 30 min. The solid material was collected using filtration. It yielded 16.2 g.

Preparation of 5-({3-Amino-5-[N-(6-sulfonaphthyl)carbamoyl]phenyl}carbonylamino)-naphthalene-2-sulfonic Acid (Compound 5)

7.00 g (31.0 mmol) of tin(II) chloride dihydrate was dissolved in 35 mL concentrated HCl and cooled to 0–5° C. in an ice bath. It was added to 7.5 g (9.6 mmol) of 4 in one portion. The mixture was stirred vigorously at room temperature for 2–3 hrs, then it was cooled in an ice bath. The white solid material was collected by filtration and washed with concentrated HCl (15 mL×3), 6 N HCl (15 mL×3), and 1 N HCl (20 mL×4). The solid was then dried in a desiccator and yielded 5.65 g.

Preparation of 5-({3-[(3-Methylphenyl)carbonylamino]-5-[N-(6-sulfonaphthyl)carbamoyl]-phenyl}carbonylamino)naphthalene-2-sulfonic Acid (Compound 7)

100 mg (0.17 mmol) of compound 5 was suspended in 5 mL of pyridine and 2 mL sulfolane and added 0.030 mL (0.23 mmol) of 3-methylbenzoyl chloride. It was stirred in room temperature for about 16 hrs. The reaction mixture became a clear solution and a solid material was precipitated out by tetrahydrofuran (THF) (100 mL). The solid material was collected using filtration and washed with THF three times. This afforded 8.0 mg of an off white powder.

Example 2

Synthesis of 5-({3-[(3-Methylphenyl)carbonylamino]-5-[N-(6-sulfonaphthyl)-carbamoyl]phenyl}carbonylamino)naphthalene-2-sulfonic Acid (Compound 7)

To 100 mg (0.17 mmol) of compound 5 suspended in 5 mL of pyridine and 2 mL of sulfolane was added 23 µL (0.172 mmol) of 3-methylbenzoyl chloride. The reaction was allowed to stir at ambient temperature for 16 hr. An additional 12 µL (0.085 mmol) of 3-methylbenzoyl chloride was added and the reaction allowed to stir for an additional 2 hr. Excess acid chloride was quenched by the addition of 0.5 mL of methanol. The reaction product was precipitated upon addition of THF (100 mL) and collected by vacuum filtration to provide 78 mg of the desired compound. The products were identified by $^1H$ NMR and mass spectroscopy and purity was assessed by RP-HPLC.

Example 3

Synthesis of 2-(N-{3,5-bis[N-(6-Sulfonaphthyl)carbamoyl]phenyl}carbamoyl)benzoic Acid (Compound 17)

To 100 mg (0.17 mmol) of compound 5 dissolved in 10 mL of dimethylformamide was added 50 mg (0.337 mmol) of phthalic anhydride. The reaction was allowed to stir at ambient temperature for 16 hr. An additional 25 mg (0.17 mmol) of phthalic anhydride was added and the reaction allowed to stir for an additional 24 hr. The reaction product was precipitated upon addition of THF (100 mL) and collected by vacuum filtration to yield 74 mg of the desired compound. The product was identified by $^1H$ NMR and mass spectroscopy and purity was assessed by RP-HPLC.

Example 4

Synthesis of Additional Compounds of Formula V

The following compounds shown in Table 1 were prepared using procedures similar to those outlined in Examples 1–3. The procedures described in Examples 1–3 can be readily modified by those skilled in the art to generate a wide array of compounds of formula V. For instance, the use of various, alternative acid chlorides instead of compound 6, in Reaction Scheme 1 of Example 1 would produce a variety of different compounds of formula V.

TABLE 1

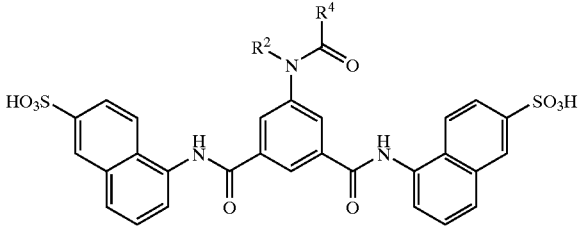

| Compound | R⁴ | R² |
|---|---|---|
| 7 | 3-methylphenyl | H |
| 8 | 4-methylphenyl | H |
| 9 | 4-methoxyphenyl | H |
| 10 | 3-chlorophenyl | H |
| 11 | 3-fluorophenyl | H |
| 12 | 4-fluorophenyl | H |
| 13 | 3-methoxyphenyl | H |
| 14 | 4-nitrophenyl | H |
| 15 | 3-nitrophenyl | H |
| 16 | 3-nitro-4-methyl-phenyl | H |
| 17 | 2-carboxyphenyl | H |
| 18 | 4,5-dichloro-2-carboxyphenyl | H |
| 19 | 4-chlorophenyl | H |
| 20 | 3,6-dichloro-2-carboxyphenyl | H |
| 21 | 2-carboxy-3-hydroxyphenyl | H |
| 22 | phenyl | H |
| 23 | methyl | H |
| 24 | 2-naphthyl | H |
| 25 | 1-naphthyl | H |
| 26 | 2-carboxy-1-aminoethyl | H |
| 27 | 2-carboxy-1-phenylethyl | H |
| 28 | 2-carboxy-2-phenylethyl | H |
| 29 | 2-sulfophenyl | H |
| 30 | 3-carboxyphenyl | H |
| 31 | 4-carboxyphenyl | H |
| 32 | 2-carboxyethyl | H |
| 33 | cyclohexyl | H |
| 34 | 2-furyl | H |
| 35 | 4-pyridyl | H |
| 36 | 3-pyridyl | H |
| 37 | phenylmethyl | H |
| 38 | phenoxymethyl | H |
| 39 | 2-quinoxalyl | H |
| 40 | 4-methylphenoxymethyl | H |
| 41 | 4-methoxyphenylmethyl | H |
| 42 | 2-[(4-methylphenyl)carbamoyl]ethyl | H |
| 43 | 4-methylphenylmethyl | H |
| 44 | 3-chlorophenylmethyl | H |
| 45 | 3-amino-4-methylphenyl | H |
| 46 | (2-naphthyloxy)methyl | H |
| 47 | 7-methoxybenzo[b]furan-2-yl | H |

The IUPAC names of the compounds shown in Table 1, above, are listed below in Table 2, below. The IUPAC names were generated using Chemistry 4D Draw™ from ChemInnovation Software, Inc.

TABLE 2

| Compound | IUPAC Name |
|---|---|
| 7 | 5-({3-[(3-methylphenyl)carbonylamino]-5-[N-(6-sulfonaphthyl)carbamoyl]phenyl}carbonylamino)naphthalene-2-sulfonic acid |
| 8 | 5-({3-[(4-methylphenyl)carbonylamino]-5-[N-(6-sulfonaphthyl)carbamoyl]phenyl}carbonylamino)naphthalene-2-sulfonic acid |
| 9 | 5-({3-[(4-methoxyphenyl)carbonylamino]-5-[N-(6-sulfonaphthyl)carbamoyl]phenyl}carbonylamino)naphthalene-2-sulfonic acid |
| 10 | 5-({3-[(3-chlorophenyl)carbonylamino]-5-[N-(6-sulfonaphthyl)carbamoyl]phenyl}carbonylamino)naphthalene-2-sulfonic acid |
| 11 | 5-({3-[(3-fluorophenyl)carbonylamino]-5-[N-(6-sulfonaphthyl)carbamoyl]phenyl}carbonylamino)naphthalene-2-sulfonic acid |
| 12 | 5-({3-[(4-fluorophenyl)carbonylamino]-5-[N-(6-sulfonaphthyl)carbamoyl]phenyl}carbonylamino)naphthalene-2-sulfonic acid |

TABLE 2-continued

| Compound | IUPAC Name |
|---|---|
| 13 | 5-({3-[(3-methoxyphenyl)carbonylamino]-5-[N-(6-sulfonaphthyl)carbamoyl]phenyl}carbonylamino)naphthalene-2-sulfonic acid |
| 14 | 5-({3-[(4-nitrophenyl)carbonylamino]-5-[N-(6-sulfonaphthyl)carbamoyl]phenyl}carbonylamino)naphthalene-2-sulfonic acid |
| 15 | 5-({3-[(3-nitrophenyl)carbonylamino]-5-[N-(6-sulfonaphthyl)carbamoyl]phenyl}carbonylamino)naphthalene-2-sulfonic acid |
| 16 | 5-({3-[(3-nitro-4-methylphenyl)carbonylamino]-5-[N-(6-sulfonaphthyl)carbamoyl]phenyl}carbonylamino)naphthalene-2-sulfonic acid |
| 17 | 2-(N-{3,5-bis[N-(6-sulfonaphthyl)carbamoyl]phenyl}carbamoyl)benzoic acid |
| 18 | 2-(N-{3,5-bis[N-(6-sulfonaphthyl)carbamoyl]phenyl}carbamoyl)-4,5-dichlorobenzoic acid |
| 19 | 5-({3-[(4-chlorophenyl)carbonylamino]-5-[N-(6-sulfonaphthyl)carbamoyl]phenyl}carbonylamino)naphthalene-2-sulfonic acid |
| 20 | 2-(N-{3,5-bis[N-(6-sulfonaphthyl)carbamoyl]phenyl}carbamoyl)-3,5-dichlorobenzoic acid |
| 21 | 2-(N-{3,5-bis[N-(6-sulfonaphthyl)carbamoyl]phenyl}carbamoyl)-6-hydroxybenzoic acid |
| 22 | 5-({3-(phenylcarbonylamino)-5-[N-(6-sulfonaphthyl)carbamoyl]phenyl}carbonylamino)naphthalene-2-sulfonic acid |
| 23 | 5-({3-(acetylamino)-5-[N-(6-sulfonaphthyl)carbamoyl]phenyl}carbonylamino)naphthalene-2-sulfonic.acid |
| 24 | 5-({3-(2-naphthylcarbonylamino)-5-[N-(6-sulfonaphthyl)carbamoyl]phenyl}carbonylamino)naphthalene-2-sulfonic acid |
| 25 | 5-({3-(1-naphthylcarbonylamino)-5-[N-(6-sulfonaphthyl)carbamoyl]phenyl}carbonylamino)naphthalene-2-sulfonic acid |
| 26 | (3S)-3-amino-3-(N-{3,5-bis[N-(6-sulfonaphthyl)carbamoyl]phenyl}carbamoyl)propanoic acid |
| 27 | 3-(N-{3,5-bis[N-(6-sulfonaphthyl)carbamoyl]phenyl}carbamoyl)-3-phenylpropanoic acid |
| 28 | 3-(N-{3,5-bis[N-(6-sulfonaphthyl)carbamoyl]phenyl}carbamoyl)-2-phenylpropanoic acid |
| 29 | 5-({5-[N-(6-sulfonaphthyl)carbamoyl]-3-[(2-sulfophenyl)carbonylamino]phenyl}carbonylamino)naphthalene-2-sulfonic acid |
| 30 | 3-(N-{3,5-bis[N-(6-sulfonaphthyl)carbamoyl]phenyl}carbamoyl)benzoic acid |
| 31 | 4-(N-{3,5-bis[N-(6-sulfonaphthyl)carbamoyl]phenyl}carbamoyl)benzoic acid |
| 32 | 3-(N-{3,5-bis[N-(6-sulfonaphthyl)carbamoyl]phenyl}carbamoyl)propanoic acid |
| 33 | 5-({3-(cyclohexylcarbonylamino)-5-[N-(6-sulfonaphthyl)carbamoyl]phenyl}carbonylamino)naphthalene-2-sulfonic acid |
| 34 | 5-({3-(2-furylcarbonylamino)-5-[N-(6-sulfonaphthyl)carbamoyl]phenyl}carbonylamino)naphthalene-2-sulfonic acid |
| 35 | 5-({3-(4-pyridylcarbonylamino)-5-[N-(6-sulfonaphthyl)carbamoyl]phenyl}carbonylamino)naphthalene-2-sulfonic acid |
| 36 | 5-({3-(3-pyridylcarbonylamino)-5-[N-(6-sulfonaphthyl)carbamoyl]phenyl}carbonylamino)naphthalene-2-sulfonic acid |
| 37 | 5-({3-(2-phenylacetylamino)-5-[N-(6-sulfonaphthyl)carbamoyl]phenyl}carbonylamino)naphthalene-2-sulfonic acid |
| 38 | 5-({3-(2-phenoxyacetylamino)-5-[N-(6-sulfonaphthyl)carbamoyl]phenyl}carbonylamino)naphthalene-2-sulfonic acid |
| 39 | 5-({3-(2-oxo-2-(2-quinolyl)acetylamino)-5-[N-(6-sulfonaphthyl)carbamoyl]phenyl}carbonylamino)naphthalene-2-sulfonic acid |
| 40 | 5-({3-[2-(4-methylphenoxy)acetylamino]-5-[N-(6-sulfonaphthyl)carbamoyl]phenyl}carbonylamino)naphthalene-2-sulfonic acid |
| 41 | 5-({3-[2-(4-methoxyphenyl)acetylamino]-5-[N-(6-sulfonaphthyl)carbamoyl]phenyl}carbonylamino)naphthalene-2-sulfonic acid |
| 42 | 5-[(3-{3-[N-(4-methylphenyl)carbamoyl]propanoylamino}-5-[N-(6-sulfonaphthyl)carbamoyl]phenyl)carbonylamino]naphthalene-2-sulfonic acid |
| 43 | 5-({3-[2-(4-methylphenyl)acetylamino]-5-[N-(6-sulfonaphthyl)carbamoyl]phenyl}carbonylamino)naphthalene-2-sulfonic acid |
| 44 | 5-({3-[2-(3-chlorophenyl)acetylamino]-5-[N-(6-sulfonaphthyl)carbamoyl]phenyl}carbonylamino)naphthalene-2-sulfonic acid |
| 45 | 5-({5-[(3-amino-4-methylphenyl)carbonylamino]-3-[N-(6-sulfonaphthyl)carbamoyl]phenyl}carbonylamino)naphthalene-2-sulfonic acid |
| 46 | 5-({5-(2-(2-naphthyloxy)acetylamino)-3-[N-(6-sulfonaphthyl)carbamoyl]phenyl}carbonylamino)naphthalene-2-sulfonic acid |
| 47 | 5-({5-[(7-methoxybenzo[d]furan-2-yl)carbonylamino]-3-[N-(6-sulfonaphthyl-carbamoyl]phenyl}carbonylamino)naphthalene-2-sulfonic acid |

Example 5

Synthesis of 5-[(3-{[(4-Chlorophenyl)sulfonyl]-amino}-5-[N-(6-sulfonaphthyl)carbamoyl]phenyl) carbonylamino]naphthalene-2-sulfonic Acid (Compound 50)

To 100 mg (0.17 mmol) of compound 5 suspended in 5 mL of pyridine and 2 mL of sulfolane was added 36 mg (0.172 mmol) of 4-chlorobenzenesulfonyl chloride. The reaction was allowed to stir at ambient temperature for 16 hr. An additional 18 mg (0.085 mmol) of the 4-chlorobenzenesulfonyl chloride was added and the reaction allowed to stir for an additional 2 hr. The reaction product was precipitated upon addition of THF and collected by vacuum filtration. The product was identified by $^1$H NMR and mass spectroscopy and purity was assessed by RP-HPLC.

Example 6

Synthesis of Additional Compounds of Formula VI

By modifying the synthesis described in Example 5 using procedures well known in the art, the compounds listed in Table 3 were prepared.

TABLE 3

| Compound | R⁴ | R² |
|---|---|---|
| 48 | phenyl | H |
| 49 | 2-naphthyl | H |
| 50 | 4-Chlorophenyl | H |
| 51 | 4-fluorophenyl | H |
| 52 | 4-methoxyphenyl | H |
| 53 | 4-methylphenyl | H |
| 54 | 1-naphthyl | H |
| 55 | 2,4,6-trimethylphenyl | H |
| 56 | phenylmethyl | H |

The IUPAC names of the compounds shown in Table 3, above, are listed below if Table 4, below. The IUPAC names were generated using Chemistry 4D Draw™ from ChemInnovation Software, Inc.

TABLE 4

| Compound | IUPAC Name |
|---|---|
| 48 | 5-({3-[(phenylsulfonyl)amino]-5-[N-(6-sulfonaphthyl)carbamoyl]phenyl}carbonylamino)naphthalene-2-sulfonic acid |
| 49 | 5-({3-[(2-naphthylsulfonyl)amino]-5-[N-(6-sulfonaphthyl)carbamoyl]phenyl}carbonylamino)naphthalene-2-sulfonic acid |
| 50 | 5-[(3-{[(4-chlorophenyl)sulfonyl]amino}-5-[N-(6-sulfonaphthyl)carbamoyl]phenyl)carbonylamino]naphthalene-2-sulfonic acid |
| 51 | 5-[(3-{[(4-fluorophenyl)sulfonyl]amino}-5-[N-(6-sulfonaphthyl)carbamoyl]phenyl)carbonylamino]naphthalene-2-sulfonic acid |
| 52 | 5-[(3-{[(4-methoxyphenyl)sulfonyl]amino}-5-[N-(6-sulfonaphthyl)carbamoyl]phenyl)carbonylamino]naphthalene-2-sulfonic acid |
| 53 | 5-[(3-{[(4-methylphenyl)sulfonyl]amino}-5-[N-(6-sulfonaphthyl)carbamoyl]phenyl)carbonylamino]naphthalene-2-sulfonic acid |
| 54 | 5-({3-[(1-naphthylsulfonyl)amino]-5-[N-(6-sulfonaphthyl)carbamoyl]phenyl}carbonylamino)naphthalene-2-sulfonic acid |
| 55 | 5-[(3-{[(2,4,6-trimethylphenyl)sulfonyl]amino}-5-[N-(6-sulfonaphthyl)carbamoyl]phenyl)carbonylamino]naphthalene-2-sulfonic acid |
| 56 | 5-[(3-{(benzylsulfonyl]amino}-5-[N-(6-sulfonaphthyl)carbamoyl]phenyl)carbonylamino]naphthalene-2-sulfonic acid |

Example 7

Preparation of 5-[(3-{[(2-Chlorophenyl)amino]carbonylamino}-5-[N-(6-sulfonaphthyl)carbamoyl]phenyl)carbonylamino]naphthalene-2-sulfonic Acid (Compound 59)

To 100 mg (0.17 mmol) of compound 5 dissolved in 10 mL of dimethylformamide and 1 mL of pyridine was added 25 µL (0.207 mmol) of 2-chlorophenyl isocyanate. The reaction was allowed to stir at ambient temperature for 16 hr. An additional 12 µL (0.103 mmol) of 2-chlorophenyl isocyanate was added and the reaction allowed to stir for an additional 2 hr. The reaction product was precipitated upon addition of THF and collected by vacuum filtration to provide 57 mg of the desired compound. The product was identified by $^1$H NMR and mass spectroscopy and purity was assessed by RP-HPLC.

Example 8

Synthesis of Additional Compounds of Formula VII

By modifying the synthesis described in Example 7 using procedures well known in the art, the compounds shown in Table 5 were prepared.

TABLE 5

| Compound | R⁴ | R² |
|---|---|---|
| 57 | 3-chlorophenyl | H |
| 58 | 4-chlorophenyl | H |
| 59 | 2-chlorophenyl | H |
| 60 | 2-methylphenyl | H |
| 61 | 3-methylphenyl | H |

TABLE 5-continued

| Compound | R⁴ | R² |
|---|---|---|
| 62 | 4-methylphenyl | H |
| 63 | 2-methoxyphenyl | H |
| 64 | 3-methoxyphenyl | H |
| 65 | 4-methoxyphenyl | H |

TABLE 5-continued

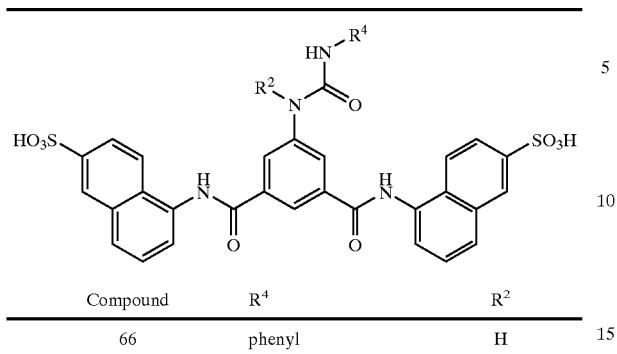

| Compound | R⁴ | R² |
|---|---|---|
| 66 | phenyl | H |

The IUPAC names of the compounds shown in Table 5, above, are listed below in Table 6, below. The IUPAC names were generated using Chemistry 4D Draw™ from ChemInnovation Software, Inc.

TABLE 6

| Compound | IUPAC Name |
|---|---|
| 57 | 5-[(3-{[(3-chlorophenyl)amino]carbonylamino}-5-[N-(6-sulfonaphthyl)carbamoyl[phenyl)carbonylamino]naphthalene-2-sulfonic acid |
| 58 | 5-[(3-{[(4-chlorophenyl)amino]carbonylamino}-5-[N-(6-sulfonaphthyl)carbamoyl[phenyl)carbonylamino]naphthalene-2-sulfonic acid |
| 59 | 5-[(3-{[(2-chlorophenyl)amino]carbonylamino}-5-[N-(6-sulfonaphthyl)carbamoyl[phenyl)carbonylamino]naphthalene-2-sulfonic acid |
| 60 | 5-[(3-{[(2-methylphenyl)amino]carbonylamino}-5-[N-(6-sulfonaphthyl)carbamoyl[phenyl)carbonylamino]naphthalene-2-sulfonic acid |
| 61 | 5-[(3-{[(3-methylphenyl)amino]carbonylamino}-5-[N-(6-sulfonaphthyl)carbamoyl[phenyl)carbonylamino]naphthalene-2-sulfonic acid |
| 62 | 5-[(3-{[(4-methylphenyl)amino]carbonylamino}-5-[N-(6-sulfonaphthyl)carbamoyl]phenyl)carbonylamino]naphthalene-2-sulfonic acid |
| 63 | 5-[(3-{[(2-methoxyphenyl)amino]carbonylamino}-5-[N-(6-sulfonaphthyl)carbamoyl]phenyl)carbonylamino]naphthalene-2-sulfonic acid |
| 64 | 5-[(3-{[(3-methoxyphenyl)amino]carbonylamino}-5-[N-(6-sulfonaphthyl)carbamoyl]phenyl)carbonylamino]naphthalene-2-sulfonic acid |
| 65 | 5-[(3-{[(4-methoxyphenyl)amino]carbonylamino}-5-[N-(6-sulfonaphthyl)carbamoyl]phenyl)carbonylamino]naphthalene-2-sulfonic acid |
| 66 | 5-({3-[(phenylamino)carbonylamino]-5-[N-(6-sulfonaphthyl)carbamoyl]phenyl}carbonylamino)naphthalene-2-sulfonic acid |

Example 9

Synthesis of 5-({3-[(3-Chlorophenyl)carbonylamino]-5-[N-(6-hydroxynaphthyl)carbamoyl]phenyl}carbonylamino)naphthalene-2-sulfonic Acid (Compound 82)

Compound 82 was synthesized according to the procedures outlined in Reaction Scheme II, III, and IV and as described below.

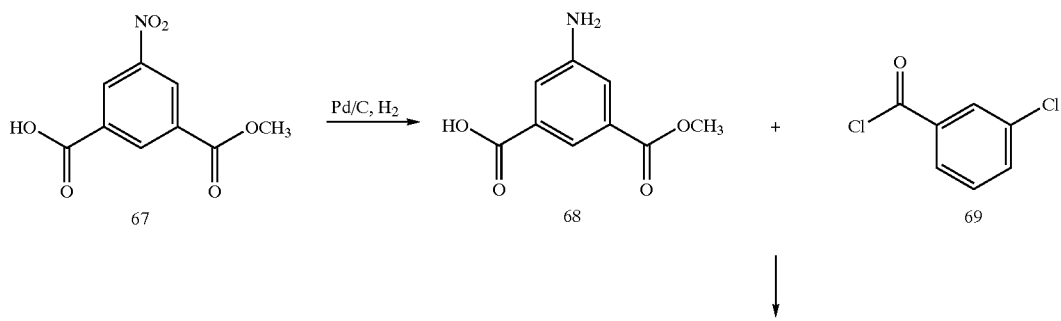

Reaction Scheme II

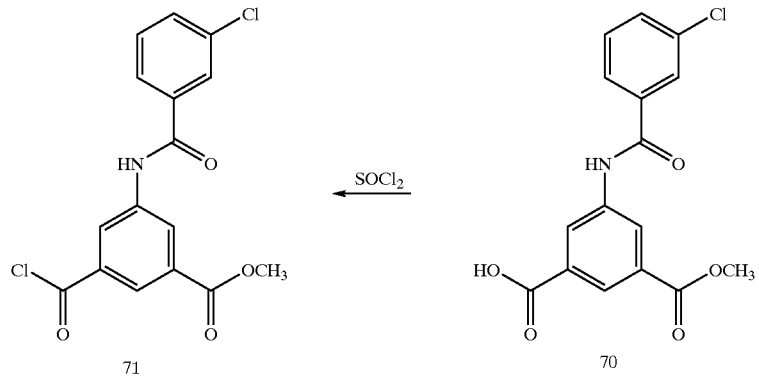

Preparation of 3-Amino-5-(methoxycarbonyl)benzoic Acid (Compound 68)

To 2.75 g of mono-methyl 5-nitroisophthalate (5-(methoxycarbonyl)-3-nitrobenzoic acid), compound 67, dissolved in 30 mL of THF was added 100 mg of 10% palladium on carbon. The reaction was placed in a Parr hydrogenator under a $H_2$ atmosphere of 45 psi and shaken for 16 hr. The solid palladium catalyst was removed by vacuum filtration through celite and 5 mL of 1N HCl in diethyl ether was added to the filtrate. After sitting for 12 hr, the solid was collected by vacuum filtration and was washed with ethyl acetate. This provided 1.82 g of the desired product. The product was identified by $^1H$ NMR and mass spectroscopy and purity was assessed by RP-HPLC.

Preparation of 3-[(3-Chlorophenyl)carbonylamino]-5-(methoxycarbonyl)benzoic Acid (Compound 70)

To 0.576 g (2.49 mmol) of compound 68 was added 10 mL of THF, 10 mL of water, and 2.6 mL of a 1N aqueous solution of sodium hydroxide. To this reaction solution was added, alternately in small portions, a solution of 341 μL (2.74 mmol) of 3-chlorobenzoyl chloride (compound 69) in 5 mL of THF and 2.6 mL of a 1N aqueous solution of sodium hydroxide. During the additions, the pH of the reaction solution was checked by pH paper and the reaction was kept at a pH greater than 8. After complete addition, TLC indicated some compound 68 remained. The above procedure was repeated using 150 μL (1.21 mmol) of 3-chlorobenzoyl chloride (69) in 5 mL THF and enough 1N aqueous sodium hydroxide to maintain a reaction solution pH above 8. After TLC analysis indicated complete consumption of compound 68, the reaction was extracted with ethyl acetate and 0.5 N aqueous sodium bicarbonate. Then, the aqueous layer was acidified with 6 N HCl and extracted with ethyl acetate. The organic layer was dried ($MgSO_4$), filtered, and volatiles removed in vacuo. The resulting residue was treated with ethyl acetate/diethyl ether 50/50 to form a white solid that was collected by vacuum filtration. This provided 0.604 g of the desired product. The product was identified by $^1H$ NMR and mass spectroscopy and purity was assessed by RP-HPLC.

Preparation of Methyl 3-(Chlorocarbonyl)-5-[(3-Chlorophenyl)carbonylamino]benzoate (Compound 71)

To 0.319 g (0.96 mmol) of compound 70 was added 8 mL of thionyl chloride and the resulting suspension was allowed to stir at ambient temperature for 2 hr. Then, 5 drops of pyridine was added. The reaction immediately became a homogenous solution. After 30 min, the volatiles were removed in vacuo and chloroform (10 mL) was added and removed in vacuo two times. This gave a solid product that was used without characterization.

Reaction Scheme III

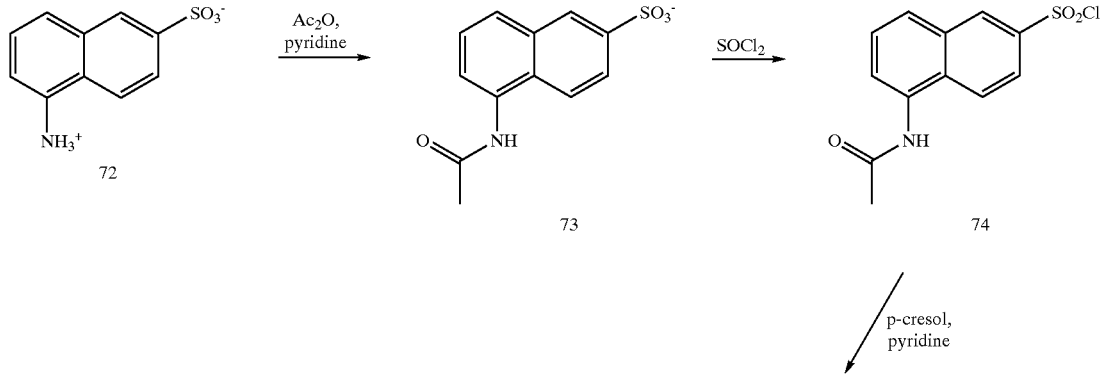

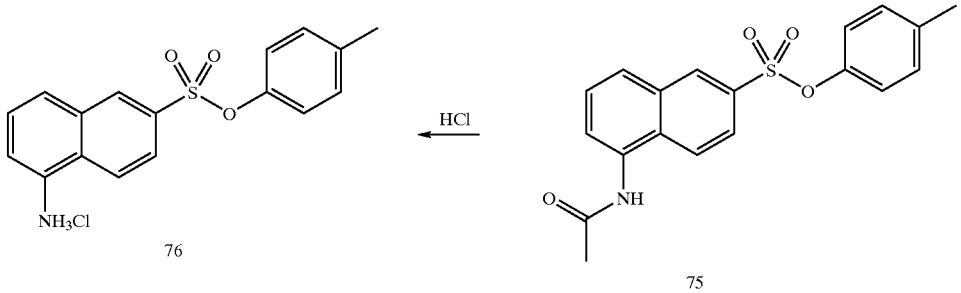

Preparation of 5-(Acetylamino)naphthalene-2-sulfonic Acid (Compound 73)

To 29.3 g (0.13 mol) of 5-amino-2-naphthalenesulfonic Acid (Compound 72) was added 40 mL of pyridine and 26 mL of acetic anhydride. The resulting suspension was allowed to stir at ambient temperature. After 24 hr, the resulting solution was diluted with 60 mL of methanol. Then, a solution of 3.6 g (0.156 mol) of sodium in 100 mL of methanol was added. After a solid precipitate began to form, 200 mL of diethyl ether was added and the suspension allowed to stir. The solid was collected by vacuum filtration and was washed with diethyl ether. This provided 38.9 g (0.11 mol) of the desired product. The product was identified by $^1$H NMR and mass spectroscopy and purity was assessed by RP-HPLC.

Preparation of 5-(Acetylamino)naphthalene-2-sulfonyl Chloride (Compound 74)

To 38.9 g (0.11 mol) of compound 73 was added 52 mL of phosphorus oxychloride, 105 mL of sulfolane, 105 mL of acetonitrile, and 4 mL of dimethylacetamide. The resulting suspension was allowed to stir at ambient temperature for 24 hr. An additional 10 mL each of sulfolane and acetonitrile were added and the reaction temperature was raised to 50° C. After 2 hr, the reaction became opaque. The reaction temperature was lowered to 25° C., and then the reaction contents were poured unto 1 L of ice. After all the ice-melted, the resulting solid was collected by vacuum filtration and was washed with cold water. This provided 33.5 g (0.11 mol) of the desired product. The product was identified by $^1$H NMR and mass spectroscopy and purity was assessed by RP-HPLC.

Preparation of 4-Methylphenyl 5-(Acetylamino) naphthalene-2-sulfonate (Compound 75)

To 15.7 mL (150 mmol) of p-cresol in 100 mL of pyridine cooled in an ice/water bath, was added half of 27.7 g (97.6 mmol) of compound 74. After 10 min, the remaining half of compound 74 was added. After another 10 min, the reaction was removed from the cold bath and allowed to warm to ambient temperature. The reaction was poured unto ice and extracted with dichloromethane. The organic layer was washed with 0.1 N aqueous HCl followed by 1.25 N aqueous NaOH. The organic layer was dried (MgSO$_4$), filtered, and volatiles removed in vacuo. The residue was recrystallized from ethyl acetate/t-butyl methyl ether to give 11.9 g (33.5 mmol) of the desired product. The volatiles were removed from the filtrate and an additional 10.5 g (29.5 mmol) of the desired product was isolated. The product was identified by $^1$H NMR and mass spectroscopy and purity was assessed by RP-HPLC.

Preparation of 4-Methylphenyl 5-Aminonaphthalene-2-sulfonate (Compound 76)

To 9.05 g (0.03 mol) of compound 75 was added 40 mL of dioxane and 120 mL of 6N aqueous HCl. The reaction suspension was heated to 75° C. for 7 hr. The resulting solution was cooled to room temperature and neutralized with 10 N aqueous sodium hydroxide to pH of 10. The reaction was extracted with ethyl acetate. The organic layer was dried (MgSO$_4$), filtered, and reduced to a small volume in vacuo. Then, 50 mL of 1N HCl in diethyl ether was added to form a solid collected by vacuum filtration. This provided 8.57 g (0.02) of the desired product. The product was identified by $^1$H NMR and mass spectroscopy and purity was assessed by RP-HPLC.

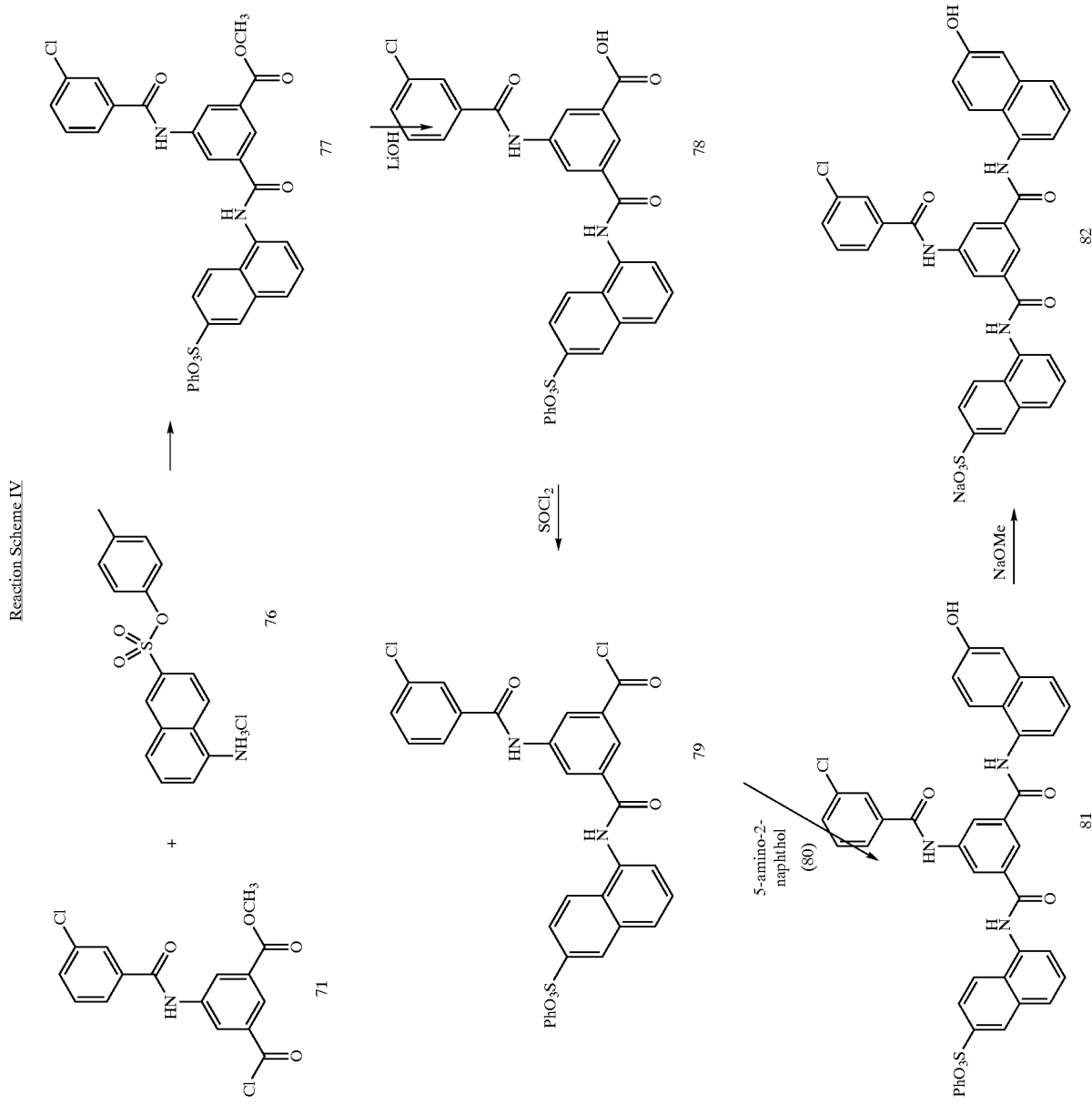

41

Preparation of Methyl 5-[(3-Chlorophenyl)carbonylamino]-3-(N-{6-[(4-methylphenyl)oxysulfonyl]naphthyl}carbamoyl)benzoate (Compound 77)

To 0.34 g (0.96 mmol) of compound 71 was added 0.33 g (0.96 mmol) of compound 76, 15 mL of dichloromethane, and 162 μL of pyridine. After 16 hr the reaction was extracted twice from ethyl acetate with 0.5 N aqueous HCl. The organic layer was then extracted with 1M aqueous sodium bicarbonate. The organic layer was dried (MgSO$_4$), filtered, and volatiles removed in vacuo. The resulting residue was stripped from dichloromethane twice and the resulting solid suspended in dichloromethane. The solid was collected by vacuum filtration. This provided 0.28 g (0.44 mmol) of the desired product. The product was identified by $^1$H NMR and mass spectroscopy and purity was assessed by RP-HPLC.

Preparation of 5-[(3-Chlorophenyl)carbonylamino]-3-(N-{6-[(4-methylphenyl)oxysulfonyl]naphthyl}carbamoyl)benzoic Acid (Compound 78)

To 0.28 g (0.44 mmol) of compound 77 was added 50 mL of THF to form a homogeneous solution. Then, 2.24 mL (2.24 mmol) of a 1N aqueous solution of lithium hydroxide was added. This produced a solid that was dissolved by the addition of 15 mL of water. After 10 hr. the reaction pH was lowered to 1 and the volatile THF removed by rotary evaporation. The resulting solid was collected by vacuum filtration. This provided 0.28 g (0.44 mmol) of the desired product. The product was identified by $^1$H NMR and mass spectroscopy and purity was assessed by RP-HPLC.

Preparation of 4-Methylphenyl 5-({3-(Chlorocarbonyl)-5-[(3-chlorophenyl)-carbonylamino]phenyl}carbonylamino)naphthalene-2-sulfonate (Compound 79)

To 23.4 mg (38.1 μmol) of compound 78 was added 0.5 mL of thionyl chloride. The suspension was allowed to stir at ambient temperature for 1 hour. Then, 1 mL of acetonitrile was added. After another hour the reaction remained a suspension so 1 mL of THF was added. The reaction solution became homogeneous within an hour. After an additional 30 min of stirring, the volatiles were removed in vacuo and the resulting residue was stripped from chloroform two times. This gave a solid product that was used without characterization.

Preparation of 4-Methylphenyl 5-({3-[(3-Chlorophenyl)carbonylamino]-5-[N-(6-hydroxynaphthyl)carbamoyl]phenyl}carbonylamino)naphthalene-2-sulfonate (Compound 81)

To 24.1 mg (38.1 μmol) of compound 79 was added 10 mL of dichloromethane followed by 16.7 mg (105 μmol) of 5-amino-2-naphthol (80) dissolved in 5 mL of 1:1 dichloromethane:THF. The reaction was allowed to stir at ambient temperature for 16 hr. The reaction was extracted with ethyl acetate and 1N aqueous HCl. The organic layer was dried (MgSO$_4$), filtered, and volatiles removed in vacuo. The resulting residue was treated with dichloromethane and diethyl ether to form a yellow solution and a solid precipitate. The solid was collected by vacuum filtration to provide 15 mg (19.9 μmol) of the desired compound. The product was identified by $^1$H NMR and mass spectroscopy and purity was assessed by RP-HPLC.

Preparation of Sodium 5-({3-[(3-Chlorophenyl)carbonylamino]-5-[N-(6-hydroxynaphthyl)carbamoyl]phenyl}carbonylamino)naphthalene-2-sulfonate 82

To 12.0 mg (15.0 μmol) of compound 81 was added 400 μL of methanol. To this stirred suspension was added 400 μL of a 1.37 M solution of sodium methoxide in methanol. The suspension quickly became homogeneous. The reaction was allowed to stir at ambient temperature for 40 hr. The reaction was acidified to pH 1 with 6 N HCl and the volatiles were removed by rotary evaporation. The resulting solid was suspended in 0.5 mL of water and the solid collected by centrifugation. This provided 10 mg (15 μmol) of the desired compound. The product was identified by $^1$H NMR and mass spectroscopy and purity was assessed by RP-HPLC.

Example 10

Synthesis of Additional Compounds of Formula VIII

By modifying the syntheses described in Example 9 using procedures well-known to the art, the compounds shown in Table 7, below, were prepared.

TABLE 7

| Compound | R$^4$ | R$^{10}$ |
|---|---|---|
| 82 | 3-chlorophenyl | 6-hydroxynaphthyl |
| 83 | 3-chlorophenyl | naphthyl |
| 84 | 4-methylphenyl | quinolinyl |

TABLE 7-continued

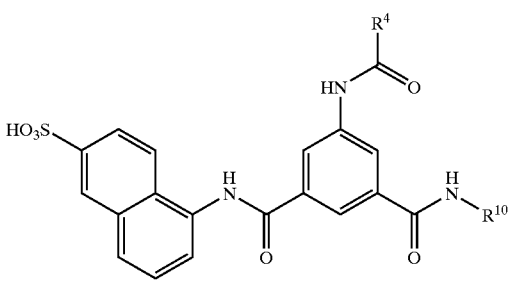

| Compound | R⁴ | R¹⁰ |
|---|---|---|
| 86 | (4-methylphenyl) | (5-methylnaphthyl-2-sulfonamide) |

The IUPAC names of the compounds shown in Table 7, above, are listed below in Table 8, below. The IUPAC names were generated using Chemistry 4D Draw™ from ChemInnovation Software, Inc.

TABLE 8

| Compound No. | IUPAC Name |
|---|---|
| 82 | Sodium 5-({3-[(3-Chlorophenyl)carbonylamino]-5-[N-(6-hydroxynaphthyl)-carbamoyl]phenyl}carbonylamino)naphthalene-2-sulfonate |
| 83 | 5-({3-[(3-Chlorophenyl)carbonylamino]-5-(N-naphthylcarbamoyl)phenyl}carbonylamino)naphthalene-2-sulfonic acid |
| 84 | 5-({3-[(4-methylphenyl)carbonylamino]-5-(N-(8-quinolyl)carbamoyl)phenyl}carbonylamino)naphthalene-2-sulfonic acid |
| 85 | (2S)-2-({5-[(4-methylphenyl)carbonylamino]-3-[N-(6-sulfonaphthyl)carbamoyl]phenyl}carbonylamino)-3-phenylpropanoic acid |
| 86 | 5-({3-[(4-methylphenyl)carbonylamino]-5-[N-(6-sulfamoylnaphthyl)carbamoyl]-phenyl}carbonylamino)naphthalene-2-sulfonic acid |

Example 11

Synthesis of 5-({5-[N-(6-Carboxynaphthyl)carbamoyl]-3-[(4-methylphenyl)-carbonylamino]phenyl}carbonylamino)naphthalene-2-carboxylic Acid (Compound 91)

Compound 91 was synthesized according to the procedures outlined in Reaction Scheme V and described below.

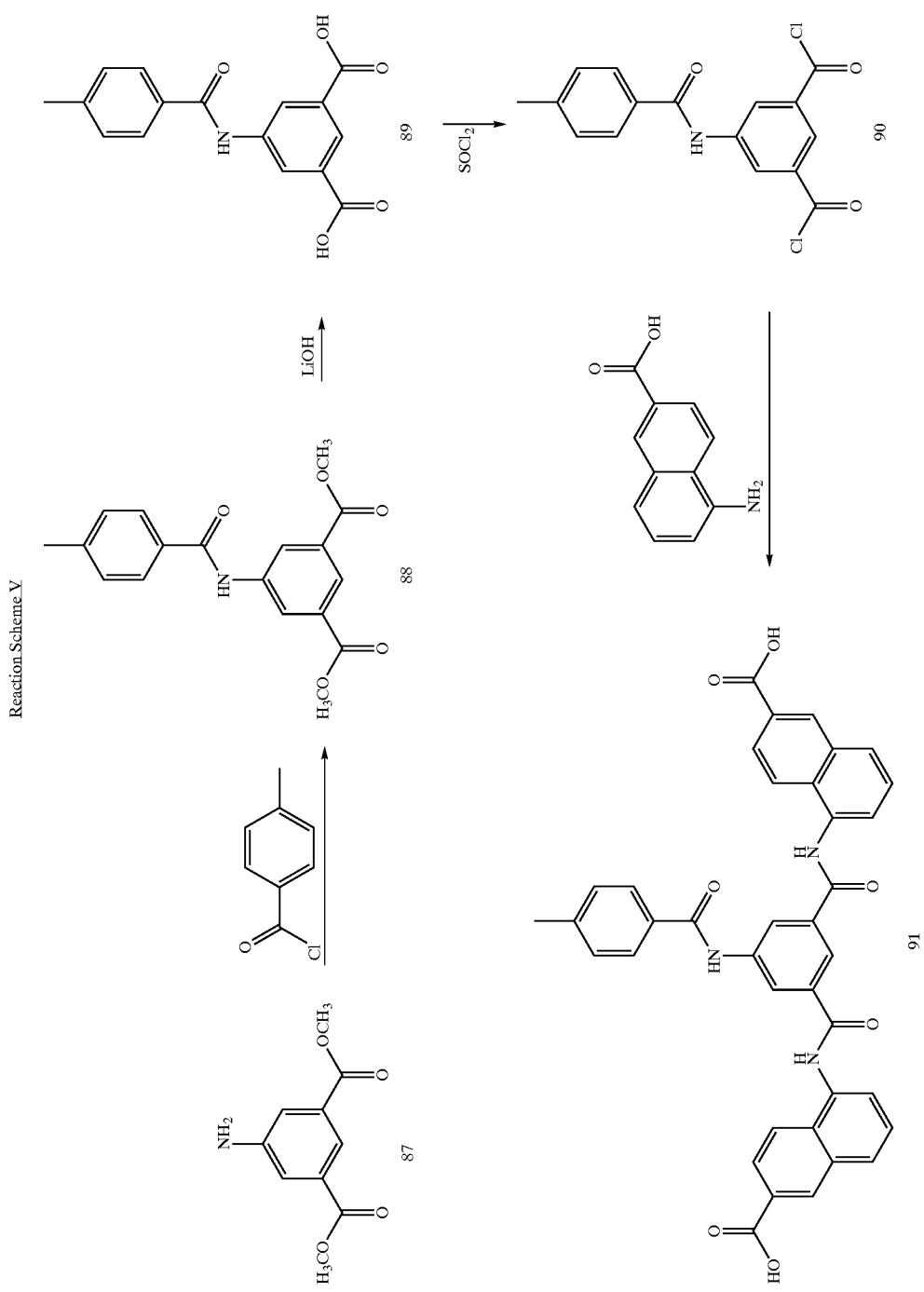

Preparation of Methyl 3-(Methoxycarbonyl)-5-[(4-methylphenyl)carbonylamino]benzoate (Compound 88)

To 1.20 g (5.74 mmol) of methyl 5-amino-3-(methoxycarbonyl)benzoate, compound 87, suspended in 50 mL of chloroform and 1.05 mL (6.00 mmol) of diisopropylethylamine was added 836 µL (6.32 mmol) of p-toluoyl chloride in 10 mL of chloroform over 30 min. The reaction was allowed to stir at ambient temperature for 2 hr. Then, another 100 µL (0.60 mmol) of diisopropylethylamine and 100 µL (0.76 mmol) of p-toluoyl chloride in 2 mL of chloroform was added. After an addition 30 min, the volatiles were removed by rotary evaporation and the resulting residue was dissolved in ethyl acetate and extracted with 0.1 N aqueous NaOH followed by extraction with water. The organic layer was dried (MgSO$_4$), filtered, and volatiles removed in vacuo. This provided 1.86 g (5.68 mmol) of the desired compound. The product was identified by $^1$H NMR and mass spectroscopy and purity was assessed by RP-HPLC.

Preparation of 5-[(4-Methylphenyl)carbonylamino]benzene-1,3-dicarboxylic Acid (Compound 89)

To 1.50 g (4.58 mmol) of compound 88 suspended in 50 mL of methanol was added 11 mL (11 mmol) of 1M aqueous LiOH. The suspension was allowed to stir at ambient temperature for 16 hr. This produced a nearly clear solution that was filtered to remove small amount of insoluble material. The methanol was removed from the filtrate by rotary evaporation and the pH of the aqueous solution was lowered to 1 with 1 N HCl. The resulting solid precipitate was collected by vacuum filtration and washed with water. This provided 1.37 g (4.57 mmol) of the desired compound. The product was identified by $^1$H NMR and mass spectroscopy and purity was assessed by RP-HPLC.

Preparation of 5-[(4-Methylphenyl)carbonylamino]benzene-1,3-dicarbonyl Chloride (Compound 90)

To 40.0 mg (13.4 mmol) of compound 89 was added 2 mL of thionyl chloride. The resulting suspension was allowed to stir for 16 hr. Then, 100 µL of pyridine was added. The reaction became a clear solution after 30 min. The reaction was allowed to stir for an additional 4 hr. The volatiles were removed in vacuo and chloroform (10 mL) was added and removed in vacuo two times. This gave a solid product that was used without characterization.

Preparation of 5-({5-[N-(6-Carboxynaphthyl)carbamoyl]-3-[(4-methylphenyl)carbonylamino]phenyl}carbonylamino)naphthalene-2-carboxylic Acid (Compound 91)

To 13.4 mmol of compound 90 dissolved in 3 mL of chloroform was added 50.0 mg (26.7 mmol) of compound (5-amino-2-naphthoic acid) (see Price, C. C.; Michel, R. H. *J. Amer. Chem. Soc.* 74, 3652 (1952)) dissolved in 4 mL of pyridine. The reaction solution was allowed to stir at ambient temperature for 16 hr. Diethyl ether was added to form a precipitate that was collected by centrifugation. This solid was dissolved in methanol and allowed to sit for 2 days. A fine precipitate was collected by centrifugation and the desired compound was purified by RP-HPLC (buffer A: 5% acetonitrile, 95% water, 0.05% TFA, buffer B: 95% acetonitrile, 5% water, 0.05% TFA). This provided 1.1 mg (1.73 µmol) of the desired compound. The product was identified by $^1$H NMR and mass spectroscopy and purity was assessed by RP-HPLC.

Example 12

Synthesis of Additional Bisnaphthylsulfonic Acids

The following additional compounds shown in Table 9 were prepared using the procedures as described in Examples 1–3.

TABLE 9

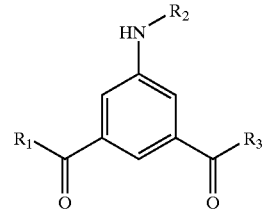

| Compound | R$^1$ | R$^2$ | R$^3$ |
|---|---|---|---|
| 92 | N-methyl-(6-sulfonaphthyl)amino | H | N-methyl-(6-sulfonaphthyl)-amino |
| 93 | N-methyl-(6-sulfonaphthyl)amino | 3-chlorobenzoyl | N-methyl-(6-sulfonaphthyl)-amino |

The IUPAC names of the compounds shown in Table 9 above are listed below in Table 10 below. The IUPAC names were generated using Chemistry 4D Draw™ from ChemInnovation Software, Inc.

TABLE 10

| Compound | IUPAC Name |
|---|---|
| 92 | 5-({3-amino-5-[N-methyl-N-(6-sulfonaphthyl)carbamoyl]-phenyl}-N-methylcarbonylamino)naphthalene-2-sulfonic acid |
| 93 | 5-({5-[(3-chlorophenyl)carbonylamino]-3-[N-methyl-N-(6-sulfonaphthyl)carbamoyl]phenyl}-N-methylcarbonylamino)naphthalene-2-sulfonic acid |

Example 13

$^{32}$-P-Cytoplasmic Kinase Domain (CKD) Autophosphorylation Assay

The complete β-kinase domain of the human insulin receptor (CKD) was expressed in, and purified from, baculovirus. CKD (4.0 µg/mL), in a solution of 50 mM Tris.HCl, 2 mM MnCl$_2$, 10 mM MgCl$_2$ (50 µl final volume), was combined with 50 µmol ATP, and 5 µCi $^{32}$P-ATP (3000 Ci/mmol.). A test compound, or the vehicle (DMSO), was added to a final DMSO concentration of 1%. The mixture was incubated for 10 minutes at room temperature. The reaction was terminated by the addition of 10 µl of 200 mM EDTA. A 30 µl volume was removed, mixed with 5 µl of 6×Laemmeli sodium dodecyl sulfate (SDS) treatment buffer, and heated to 94° C. for 5 minutes. A 20 µl aliquot was then run on an SDS-PAGE gel. The radioactivity incorporated into the CKD band is quantified by phosphorimaging of the gel, or scintillation counting of the excised bands.

The results for this assay are shown in Table 11. The potency of a compound for increasing phosphorylation is expressed as a percentage of the vehicle level.

TABLE 11

| Compound | Activity (% Control) |
|---|---|
| 7 | 93.3 |
| 8 | 130.5 |
| 9 | 125.3 |
| 10 | 123.1 |
| 11 | 94 |
| 12 | 88.6 |
| 13 | 83.7 |
| 14 | 81.7 |
| 15 | 88.2 |
| 16 | 99.9 |
| 17 | 92.7 |
| 18 | 95.3 |
| 19 | 99 |
| 20 | 84.9 |
| 21 | 104.3 |
| 22 | 75.9 |
| 23 | 86.8 |
| 24 | 89.6 |
| 25 | 83.7 |
| 26 | 91.4 |
| 27 | 161.2 |
| 28 | 84.6 |
| 29 | 75.6 |
| 30 | 84.1 |
| 31 | 159.2 |
| 32 | 109.9 |
| 33 | 122.5 |
| 34 | 119.5 |
| 35 | 105.9 |
| 36 | 123.2 |
| 37 | 113.2 |
| 38 | 84.7 |
| 39 | 96.9 |
| 40 | 130.7 |
| 41 | 136.6 |
| 42 | 116.7 |
| 43 | 124.2 |
| 44 | 124.8 |
| 48 | 114.2 |
| 49 | 109.3 |
| 50 | 123.8 |
| 51 | 133.0 |
| 52 | 111.1 |
| 53 | 105.7 |
| 54 | 46.5 |
| 55 | 121.6 |
| 56 | 102.4 |
| 57 | 109.6 |
| 58 | 106.4 |
| 59 | 120.4 |
| 60 | 97.5 |
| 61 | 114.6 |
| 62 | 102.8 |
| 63 | 94.4 |
| 64 | 58.3 |
| 65 | 85.9 |
| 66 | 115.5 |

Example 14

Glucose Transport Activity

3T3 L1 fibroblasts (ATCC) were grown in Dulbecco's modified Eagle's medium (DMEM) with 10% fetal bovine serum (FBS, medium). The cells were plated at a density of $3\times10^4$ cells/well in 24-well plates. Two days after confluence was reached, the cells were treated for 3 days with 0.5 mM isobutylmethylxanthine (IBMX), 1 μM dexamethasone, supplemented with 1.7 μM insulin. The cells were then transferred to medium with 1.7 μM insulin for 2 more days. The cells were maintained in medium for an additional 4 days. Finally the cells were serum starved overnight in 0.1% bovine serum albumin (BSA) in DMEM.

The following day, the culture medium was replaced with 150 mM NaCl, 1.7 mM KCl, 0.9 mM $CaCl_2$, 1.47 mM $K_2HPO_4$ (pH 7.4) to which was added either the experimental compounds, or their vehicle (DMSO). Insulin or its vehicle (0.01% BSA) was diluted in the assay buffer (containing test compound or vehicle, respectively) to a final concentration of 5.6 nM. After incubation for 30 min at 37° C. 5 μCi/mL $^{14}$C-2-Dixie-D-glucose was added, and the incubation was continued for additional 30 min at 37° C. The cells were then washed 3 times with ice-cold PBS/20 mM glucose and Lysol in 250 μl of lysis buffer (50 mM HEPES pH 7.6, 1% Triton X-100) for 30 min at room temperature. Radioactivity in the lysate was quantified by scintillation counting.

Once $^{14}$C-2-deoxy-D-glucose is transported into the cell it is not released. Glucose transport is, therefore, proportional to the amount of radioactivity in the lysate. The concentration of compound necessary to produce an increase in glucose transport greater than the sum of the standard deviation of the vehicle control plus the largest standard deviation of a test sample (generally 150% of the vehicle control) was recorded as the EC (effective concentration).

The results of the glucose transport activity assay are shown in Table 12, below.

TABLE 12

| Compound | $EC_{50}$ (μM) |
|---|---|
| 7 | >250 |
| 8 | 3 |
| 9 | 10 |
| 10 | 20 |
| 11 | 20 |
| 13 | 200 |
| 15 | 240 |
| 16 | 20 |
| 17 | >250 |
| 18 | >250 |
| 19 | 150 |
| 21 | >250 |
| 22 | 200 |
| 23 | >250 |
| 39 | 100 |
| 40 | >250 |
| 94 | 90 |
| 95 | 9 |

Example 15

Blood Glucose Level Determination in db/db Mice

Seven to 9 week old male db/db mice (Jackson Laboratories, Bar Harbor, Me.), were used to the study of the effects of compounds on blood glucose levels. Animals were kept in a 12 h/12 h light/dark cycle, and experiments were initiated immediately after the dark period (7:00 a.m.). Food was removed at this time and returned after the final blood glucose measurement was taken.

Insulin (0.5 U/ml, Humulin R, Catalog HI-201, Lilly, Indianapolis, Ind.) was prepared by diluting 100 U/mL stock insulin 1:200 with PBS (phosphate buffered saline, Gibco, BRL). Compounds were prepared in a vehicle of either PBS or 20% DMSO in PBS.

Five to 10 animals (average weight 40–50 g) were used in each treatment condition. The animals were injected subcutaneously with either 0.01 U insulin in PBS, followed by 0.1 mL of compound or its vehicle delivered intraperitoneally. Blood samples were taken 0 min, 15 min, 30 min, 1 hr, 2 hr and 4 hr after the administration of the drug or vehicle by tail bleeding. Glucose measurements were made with a Glucometer and Glucose strips (Bayer). The resulting data are shown in FIGS. 1 and 2.

FIG. 1 shows the effect of compound 8 in combination with insulin on blood glucose levels in db/db mice. Blood glucose levels at various time points are shown following injections either with insulin in phosphate buffered saline (PBS) or with compound 8 and insulin in PBS. The blood glucose levels are reported as the percentage of the "0-time" values.

FIG. 2 shows the effect of compound 10 in combination with insulin on blood glucose levels in db/db mice. Blood glucose levels at various time points are shown following injection of db/db mice with compound 10, its vehicle (DMSO) and insulin in PBS. Blood glucose levels at various time points following injections either with insulin in PBS or with PBS and DMSO are also shown for comparison.

Example 16

Effect on 3T3-HIR Cells

Figure 3:
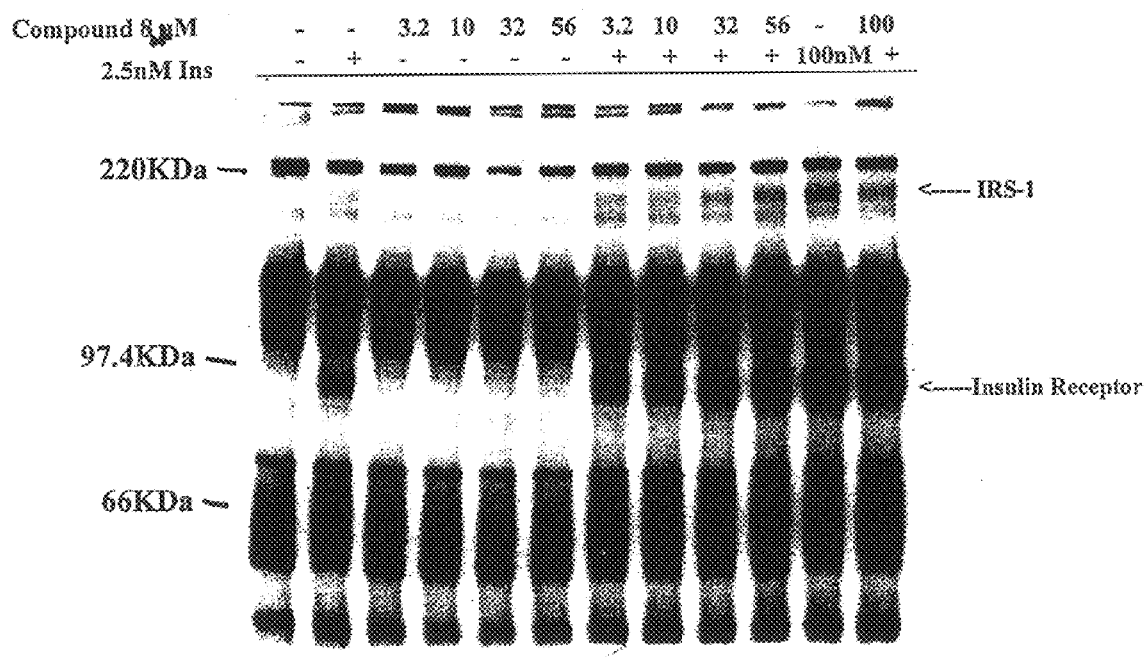
FIG. 3 shows the effect of compound 8 on 3T3 HIR cells.

3T3-HIR cells were grown in DMEM with 10% FBS in 6 well dishes. After reaching 90% confluency, the cells were serum starved with 0.1% BSA in DMEM for 16 hr. The cells were stimulated with 3.2, 10, 32, 56 and 100 μM of compound in the presence or absence of 2.5 nM insulin for 15 minutes at 37° C. The cells were lysed in the lysis buffer and 20 μg of total cell lysate from each sample was resolved in a 8% SDS-PAGE, transferred onto an Immobilon-P membrane and probed with anti-phosphotyrosine antibody. Insulin receptor 1-subunit and IRS-1 protein bands were identified and quantified by using Phosphorimager (Molecular Dynamics), with the autoradiogram shown in FIG. 3.

Example 17

Oral Pharmaceutical Composition Preparation— Solid Dosage Formulation

A pharmaceutical composition for oral administration may be prepared by combining the following:

| | % w/w |
|---|---|
| Compound of the invention | 10% |
| Magnesium stearate | 0.5% |
| Starch | 2.0% |
| hydroxypropylmethylcellulose | 1.0% |
| Microcrystalline cellulose | 86.5% |

The mixture may be compressed to tablets, or filled into hard gelatin capsules.

The tablet may be coated by applying a suspension of film former (e.g. hydroxypropylmethylcellulose), pigment (e.g. titanium dioxide) and plasticiser (e.g. diethyl phthalate) and drying the film by evaporation of the solvent. The film coat can comprise 2.0% to 6.0% of the tablet weight, preferably about 3.0%.

Example 18

Oral Pharmaceutical Composition Preparation— Capsule

A pharmaceutical composition of a compound of the invention suitable for oral administration may also be prepared by combining the following:

| | % w/w |
|---|---|
| Compound of the invention | 20% |
| Polyethylene glycol | 80% |

The medicinal compound is dispersed or dissolved in the liquid carrier, with a thickening agent added, if required. The formulation is then enclosed in a soft gelatin capsule by suitable technology.

Example 19

Pharmaceutical Composition for Parenteral Administration

A pharmaceutical composition for parenteral administration may be prepared by combining the following:

| | Preferred Level |
|---|---|
| Compound of formula I-VIII | 1.0% |
| Saline | 99.0% |

The solution is sterilized and sealed in sterile containers.

All documents cited in the above specification are herein incorporated by reference. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

We claim:

1. A compound of the formula:

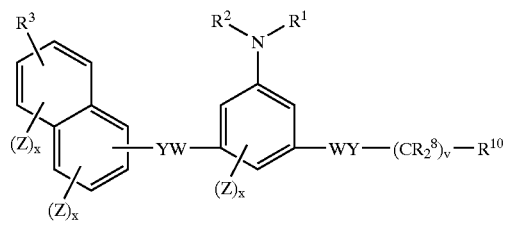

where:

$R^1$ and $R^2$ are, independently, hydrogen, alkyl, substituted alkyl, aryl, substituted aryl, —C(O)$R^4$, —C(O)O$R^4$, —C(O)N$R^4R^5$, —S(O)$_2R^4$, —S(O)$_2$O$R^4$, heteroaryl, substituted heteroaryl, heterocyclyl, substituted heterocyclyl, aryl(lower)alkyl, substituted aryl(lower)alkyl, heteroaryl(lower)alkyl, substituted heteroaryl(lower)alkyl or lower alkenyl, or $R^1$ and $R^2$ together with the conjoining nitrogen are $C_5$–$C_9$ heteroaryl, $C_3$–$C_5$ heterocyclyl, or both $R^1$ and $R^2$ are oxygen and together with the conjoining nitrogen form —NO$_2$;

$R^3$ is —SO$_2$O$R^6$, —C(C)O$R^6$, —SO$_2$N$R^6{}_2$, —C(O)NR$_2$ or tetrazolyl;

each $R^4$ and $R^5$ is, independently, hydrogen, alkyl, $R^{11}$-substituted alkyl, aryl, $R^{11}$-substituted aryl, aryl(lower)

allyl, $R^{11}$-substituted aryl(lower)alkyl, $R^{11}$-substituted heteroaryl, heteroaryl, heteroaryl(lower)alkyl, $R^{11}$-substituted heteroaryl(lower)alkyl, heterocyclyl, $R^{11}$-substituted heterocyclyl, or lower alkenyl;

each $R^6$ and $R^7$ is, independently, hydrogen or lower alkyl;

each $R^8$ is, independently, hydrogen, lower alkyl, halo-lower alkyl, nitro, halo, cyano, amino, lower alkyloxy, thio, or —C(O)OR$^9$ (where $R^9$ is lower alkyl or hydrogen);

$R^{10}$ is aryl optionally substituted with lower alkyl, halo-lower alkyl, halo, cyano, thio, nitro, amino, lower akyloxy, hydroxy, —SO$_2$OR, —SO$_2$NR, —COOR, or —CONR$_2$ (where R is hydrogen or lower alkyl);

each $R^{11}$ is, independently, aryl, substituted aryl, alkyl, substituted alkyl, substituted heteroaryl, heteroaryl, heterocyclyl, substituted heterocyclyl, lower alkenyl, nitro, halo, cyano, —OR$^{12}$, —SR$^{12}$, —C(O)R$^{12}$, —OC(O)R$^{12}$, —C(O)OR$^{12}$, —NR$^{12}$$_2$, —C(O)NR$^{13}$$_2$, —NR$^{12}$C(O)R$^{13}$, —OSO$_2$R$^{12}$, —SO$_2$OR$^{12}$, —SO$_2$NR$^{12}$$_2$, or —NR$^{12}$SO$_2$R$^{12}$; and each $R^{12}$ and $R^{13}$ is, independently, hydrogen, lower alkyl, substituted lower alkyl, aryl, substituted aryl, heteroaryl, substituted heteroaryl, heteroaryl(lower)alkyl, substituted heteroaryl(lower)alkyl, heterocyclyl, substituted heterocyclyl, aryl(lower)alkyl, or substituted aryl(lower)alkyl;

the linker —WY— between the naphthyl and phenyl intersects the A ring of the naphthyl and is, independently, —C(O)NR$^7$—, —NR$^7$C(O)—, —C(O)O—, —OC(O)—, —CH=CH—, —NR$^7$CH$_2$—, —CH$_2$NR$^7$—, —NR$^7$C(O)NR$^7$—, —NR$^7$C(O)O—, —OC(O)NR$^7$—, —NR$^7$SO$_2$O—, —OSO$_2$NR$^7$—, —OC(O)O—, —SO$_2$NR$^7$—, —NR$^7$SO$_2$—, —OSO$_2$—, or —SO$_2$O—;

each Z is, independently, alkyl, substituted alkyl, cyano, halo, nitro, —SR$^{14}$, —OR$^{14}$, or —NR$^{14}$$_2$; and each $R^{14}$ is, independently, hydrogen, lower alkyl, or substituted lower alkyl;

each x and v is, independently, 0, 1, 2 or 3;

provided that if $R^1$ or $R^2$ is —C(O)NR$^4$R$^5$, then $R^{13}$ is neither aryl nor substituted aryl, where a heteroaryl is selected from the group consisting of thienyl, furyl, pyrrolyl, indolyl, isobenzofuranyl, isoquinolyl, pyridyl, and quinolyl, or a heterocyclyl is selected from the group consisting of tetrahydrofuranyl, tetrahydropyranyl, and piperidinyl, as a single stereoisomer or mixture of stereoisomers, or a pharmaceutically acceptable salt thereof.

2. A compound of claim 1, where $R^1$ is —C(O)R$^4$, —C(O)NR$^4$R$^5$, or —SO$_2$R$^4$; and $R^2$ is hydrogen or lower alkyl.

3. A compound of claim 2, where $R^4$ is lower alkyl, $R^{11}$-substituted lower alkyl, aryl, $R^{11}$-substituted aryl, aryl(lower)alkyl, $R^{11}$-substituted aryl(lower)alkyl, heteroaryl(lower)alkyl, or heteroaryl; and $R^5$ is hydrogen or lower alkyl.

4. A compound of claim 3, where each $R^{11}$ is, independently, aryl, $R^{15}$-substituted aryl, lower alkyl, $R^{15}$-substituted lower alkyl, heteroaryl, nitro, halo, cyano, amino, thio, —OR$^{12}$, —C(O)R$^{12}$, —OC(O)R$^{12}$, —C(O)OR$^{12}$, —C(O)NR$^{13}$$_2$, or —NR$^{12}$C(O)R$^{13}$;

each $R^{12}$ and $R^{13}$ is, independently, hydrogen, lower alkyl, $R^{15}$-substituted lower alkyl, aryl, $R^{15}$-substituted aryl, heteroaryl, heteroaryl(lower)alkyl, aryl(lower)alkyl, or $R^{15}$-substituted aryl(lower)alkyl; and each $R^{15}$ is, independently, halo, thio, amino, nitro, cyano, hydroxy, lower alkyl, halo-lower alkyl, or lower alkyloxy.

5. A compound of claim 1, where each $R^3$ is, independently, —SO$_2$OR$^6$, —SO$_2$NR$^6$$_2$, —C(O)OR$^6$, —C(O)NR$^6$$_2$ or tetrazolyl.

6. A compound of claim 5, where each $R^3$ is, independently, —SO$_2$OH, —C(O)OH, or tetrazolyl.

7. A compound of claim 1, where $R^{10}$ is naphthyl or phenyl, each optionally substituted with lower alkyl, halo-lower alkyl, halo, cyano, thio, nitro, amino, lower akyloxy, hydroxy, —SO$_2$OR, —SO$_2$NR$_2$, —COOR, or —CONR$_2$ (where R is hydrogen or lower alkyl).

8. A compound of claim 1, where each —WY— linker is, independently, —C(O)NR$^7$—, —NR$^7$C(O)—, —SO$_2$NR$^7$—, —NR$^7$SO$_2$—, or —NR$^7$C(O)NR$^7$—.

9. A compound of claim 8 where each —WY— linker is —C(O)NR$^7$—.

10. A compound of claim 1 where each Z is lower alkyl, halo-lower alkyl, lower alkyloxy, cyano, halo, thio, amino, nitro, or hydroxy.

11. A compound of claim 1, where each x is 0.

12. A compound of claim 1, where v is 1, 2, or 3.

13. A compound of claim 1, where v is zero.

14. A compound of claim 2, where $R^2$ is hydrogen;

$R^4$ is phenyl or naphthyl, each optionally substituted with lower alkyl, lower alkoxy, halo, nitro, carboxy, hydroxy, or sulfo;

lower alkyl optionally substituted with phenyl, phenyloxy, lower alkylphenyloxy, lower alkoxyphenyl, lower alkylphenyl, halophenyl, amino, carboxy, naphthyloxy, or lower alkylphenylcarbamoyl; cyclohexyl, furyl, pyridyl, quinoxalyl, or benzofuranyl optionally substituted with lower alkoxy.

15. A compound of claim 1, which is a compound of the formula:

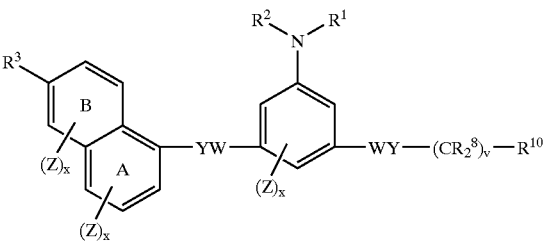

as a single stereoisomer or mixture of stereoisomers, or a pharmaceutically acceptable salt thereof.

16. A compound of claim 1, which is a compound of the formula:

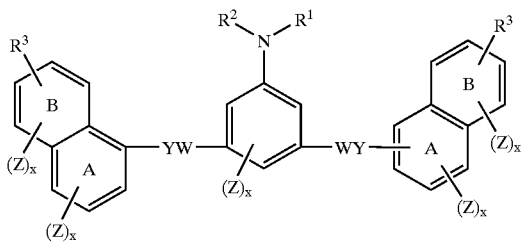

as a single stereoisomer or mixture of stereoisomers,
or a pharmaceutically acceptable salt thereof.

17. A compound of claim 1, which is a compound of the formula:

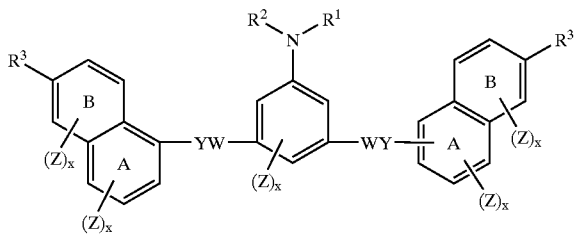

as a single stereoisomer or mixture of stereoisomers,
or a pharmaceutically acceptable salt thereof.

18. A compound of claim 1, which is a compound of the formula:

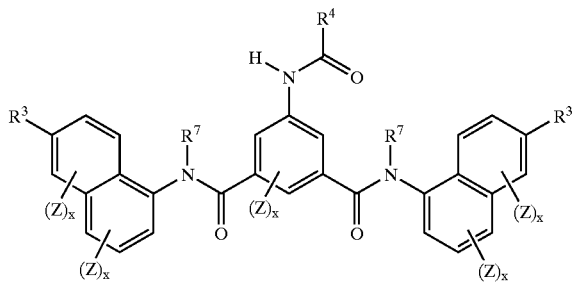

where:
$R^4$ is alkyl, $R^{11}$-substituted alkyl, aryl, $R^{11}$-substituted aryl, aryl(lower)alkyl, $R^{11}$-substituted aryl(lower)alkyl, heteroaryl(lower)alkyl, $R^{11}$-substituted heteroaryl (lower)alkyl, heterocyclyl, $R^{11}$-substituted heterocyclyl, heteroaryl, or $R^{11}$-substituted heteroaryl;

each $R^{11}$ is, independently, aryl, $R^{15}$-substituted aryl, lower alkyl, $R^{15}$-substituted lower alkyl, heteroaryl, nitro, halo, cyano, amino, thio, —$OR^{12}$, —$C(O)R^{12}$, —$OC(O)R^{12}$, —$C(O)OR^{12}$, —$C(O)NR^{13}{}_2$, or —$NR^{12}C(O)R^{13}$;

each $R^{12}$ and $R^{13}$ is, independently, hydrogen, lower alkyl, $R^{15}$-substituted lower alkyl, aryl, $R^{15}$-substituted aryl, heteroaryl, heteroaryl(lower)alkyl, aryl(lower)alkyl, or $R^{15}$-substituted aryl(lower)alkyl; and $R^{15}$ is, independently, halo, thio, amino, nitro, cyano, hydroxy, lower alkyl or lower alkyloxy;

Z is lower alkyl, halo-lower alkyl, lower alkyloxy, cyano, halo, thio, amino, nitro, or hydroxy; and x is 0, 1, or 2, as a single stereoisomer or mixture of stereoisomers,
or a pharmaceutically acceptable salt thereof.

19. A compound of claim 1, which is a compound of the formula:

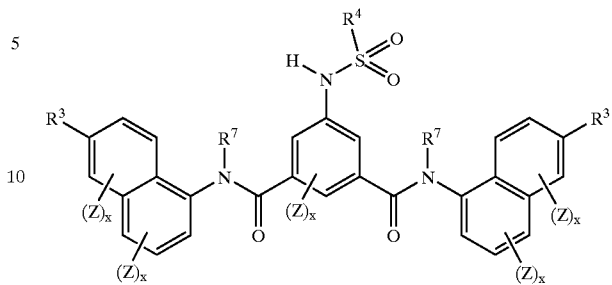

where
$R^4$ is alkyl, $R^{11}$-substituted alkyl, aryl, $R^{11}$-substituted aryl, aryl(lower)alkyl, $R^{11}$-substituted aryl(lower)alkyl, heteroaryl(lower)alkyl, $R^{11}$-substituted heteroaryl (lower)alkyl, heterocyclyl, $R^{11}$-substituted heterocyclyl, heteroaryl, or $R^{11}$-substituted heteroaryl;

each $R^{11}$ is, independently, aryl, $R^{15}$-substituted aryl, lower alkyl, $R^{15}$-substituted lower alkyl, heteroaryl, nitro, halo, cyano, amino, thio, —$OR^{12}$, —$C(O)R^{12}$, —$OC(O)R^{12}$, —$C(O)OR^{12}$, —$C(O)NR^{13}{}_2$, or —$NR^{12}C(O)R^{13}$;

each $R^{12}$ and $R^{13}$ is, independently, hydrogen, lower alkyl, $R^{15}$-substituted lower alkyl, aryl, $R^{15}$-substituted aryl, heteroaryl, heteroaryl(lower)alkyl, aryl(lower) alkyl, or $R^{15}$-substituted aryl(lower)alkyl; and $R^{15}$ is, independently, halo, thio, amino, nitro, cyano, hydroxy, lower alkyl or lower alkyloxy;

Z is lower alkyl, halo-lower alkyl, lower alkyloxy, cyano, halo, thio, amino, nitro, or hydroxy; and x is 0, 1, or 2, as a single stereoisomer or mixture of stereoisomers,
or a pharmaceutically acceptable salt thereof.

20. A compound of claim 1, which is a compound of the formula:

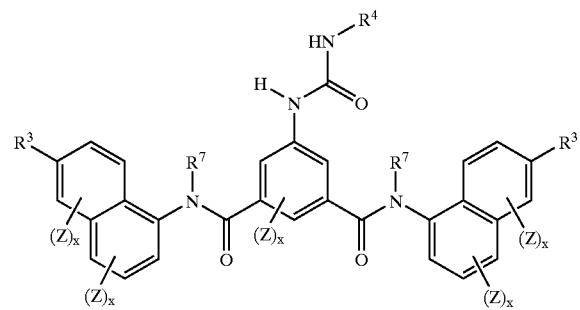

where:
$R^4$ is alkyl, $R^{11}$-substituted alkyl, aryl, $R^{11}$-substituted aryl, aryl(lower)alkyl, $R^{11}$-substituted aryl(lower)alkyl, heteroaryl(lower)alkyl, $R^{11}$-substituted heteroaryl (lower)alkyl, heterocyclyl, $R^{11}$-substituted heterocyclyl, heteroaryl, or $R^{11}$-substituted heteroaryl;

each $R^{11}$ is, independently, aryl, $R^{15}$-substituted aryl, lower alkyl, $R^{15}$-substituted lower alkyl, heteroaryl, nitro, halo, cyano, amino, thio, —$OR^{12}$, —$C(O)R^{12}$, —$OC(O)R^{12}$, —$C(O)OR^{12}$, —$C(O)NR^{13}{}_2$, or —$NR^{12}C(O)R^{13}$;

each $R^{12}$ is, independently, hydrogen, lower alkyl, $R^{15}$-substituted lower alkyl, aryl, $R^{15}$-substituted aryl, heteroaryl, heteroaryl(lower)alkyl, aryl(lower)alkyl, or R$^{15}$-substituted aryl(lower)alkyl;

each R$^{13}$ is, independently, hydrogen, lower alkyl, R$^{15}$-substituted lower alkyl, heteroaryl, heteroaryl(lower)alkyl, aryl(lower)alkyl, or R$^{15}$-substituted aryl(lower)alkyl;

R$^{15}$ is, independently, halo, thio, amino, nitro, cyano, hydroxy, lower alkyl or lower alkyloxy;

Z is lower alkyl, halo-lower alkyl, lower alkyloxy, cyano, halo, thio, amino, nitro, or hydroxy; and x is 0, 1, or 2, as a single stereoisomer or mixture of stereoisomers, or a pharmaceutically acceptable salt thereof.

21. The compound of claim 1, which is a compound of the formula:

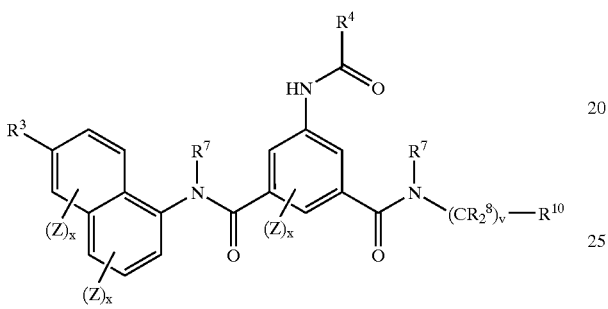

where

R$^4$ is alkyl, R$^{11}$-substituted-alkyl, aryl, R$^{11}$-substituted aryl, aryl(lower)alkyl, R$^{11}$-substituted aryl(lower)alkyl, heteroaryl(lower)alkyl, R$^{11}$-substituted heteroaryl(lower)alkyl, heterocyclyl, R$^{11}$-substituted heterocyclyl, heteroaryl, or R$^{11}$-substituted heteroaryl;

each R$^8$ is, independently, hydrogen, lower alkyl, halo-lower alkyl, nitro, halo, cyano, amino, lower alkyloxy, thio, or —C(O)R$^9$ (where R$^9$ is hydrogen or lower alkyl);

R$^{10}$ is aryl optionally substituted with lower alkyl, halo-lower alkyl, halo, cyano, thio, nitro, amino, lower akyloxy, hydroxy, —SO$_2$OR, —SO$_2$NR$_2$, —COOR, or —CONR$_2$ (where R is hydrogen or lower alkyl);

each R$^{11}$ is, independently, aryl, R$^{15}$-substituted aryl, lower alkyl, R$^{15}$-substituted lower alkyl, heteroaryl, nitro, halo, cyano, amino, thio, —OR$^{12}$, —C(O)R$^{12}$, —OC(O)R$^{12}$, —C(O)OR$^{12}$, —C(O)NR$^{13}$$_2$, or —NR$^{12}$C(O)R$^{13}$;

each R$^{12}$ and R$^{13}$ is, independently, hydrogen, lower alkyl, R$^{15}$-substituted lower alkyl, aryl, R$^{15}$-substituted aryl, heteroaryl, heteroaryl(lower)alkyl, aryl(lower)alkyl, or R$^{15}$-substituted aryl(lower)alkyl; and R$^{15}$ is, independently, halo, thio, amino, nitro, cyano, hydroxy, lower alkyl or lower alkyloxy;

Z is lower alkyl, halo-lower alkyl, lower alkyloxy, cyano, halo, thio, amino, nitro, or hydroxy; and each x is, independently, 0, 1, or 2, as a single stereoisomer or mixture of stereoisomers, or a pharmaceutically acceptable salt thereof.

22. A compound of claim 1 selected from the group consisting of:

5-({3-[(4-methylphenyl)carbonylamino]-5-[N-(6-sulfonaphthyl)carbamoyl]phenyl}carbonylamino)naphthalene-2-sulfonic acid, 5-({3-[(4-methoxyphenyl)carbonylamino]-5-[N-(6-sulfonaphthyl)carbamoyl]phenyl}carbonylamino)naphthalene-2-sulfonic acid, 5-({3-[(3-chlorophenyl)carbonylamino]-5-[N-(6-sulfonaphthyl)carbamoyl]phenyl}carbonylamino)naphthalene-2-sulfonic acid, 5-({3-[(3-nitro-4-methylphenyl)carbonylamino]-5-[N-(6-sulfonaphthyl)carbamoylphenyl}carbonyl]amino)naphthalene-2-sulfonic acid, and the pharmaceutically acceptable salts thereof.

23. A pharmaceutical composition comprising:

(a) a compound of claim 1 as an active ingredient; and (b) a pharmaceutically acceptable carrier.

24. A pharmaceutical composition for treating a mammalian disease state selected from the group consisting of hyperglycemia, type I diabetes, and type II diabetes, comprising:

(a) a pharmaceutically acceptable carrier; and (b) as an active ingredient, a compound of the formula:

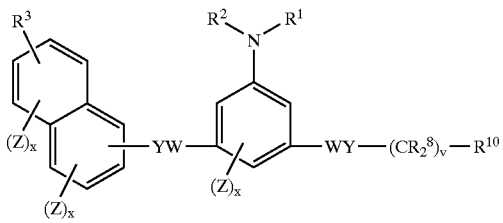

where:

R$^1$ and R$^2$ are, independently, hydrogen, alkyl, substituted alkyl, aryl, substituted aryl, —C(O)R$^4$, —C(O)OR$^4$, —C(O)NR$^4$R$^5$, —S(O)$_2$R$^4$, —S(O)$_2$OR$^4$, heteroaryl, substituted heteroaryl, hetero substituted heterocyclyl, aryl(lower)alkyl, substituted aryl(lower)alkyl heteroaryl(lower)alkyl, substituted heteroaryl(lower)alkyl, or lower alkenyl, or R$^1$ and R$^2$ together with the conjoining nitrogen are C$_5$–C$_9$ heteroaryl, C$_3$–C$_5$ heterocyclyl, or both R$^1$ and R$^2$ are oxygen and together with the conjoining nitrogen forming —NO$_2$;

R$^3$ is —SO$_2$OR$^6$, —C(O)OR$^6$, —SO$_2$NR$^6$$_2$, —C(O)NR$^6$$_2$ or tetrazolyl;

each R$^4$ and R$^5$ is, independently, hydrogen, alkyl, substituted alkyl, aryl, substituted aryl, aryl(lower)alkyl, substituted aryl(lower)alkyl, substituted heteroaryl, heteroaryl, heteroaryl(lower)alkyl, substituted heteroaryl(lower)alkyl, heterocyclyl, substituted heterocyclyl, or lower alkenyl, each R$^6$ and R$^7$ is, independently, hydrogen or lower alkyl;

each R$^8$ is, independently, hydrogen, lower alkyl, halo-lower alkyl, nitro, halo, cyano, amino, lower alkyloxy, thio, or —C(O)OR$^9$ (where R$^9$ is lower alkyl or hydrogen);

R$^{10}$ is aryl optionally substituted with lower alkyl, halo-lower alkyl, halo, cyano, thio, nitro, amino, lower akyloxy, hydroxy, —SO$_2$OR, —SO$_2$NR$_2$, —COOR, or —CONR$_2$ (where R is hydrogen or lower alkyl);

the linker —WY— between the naphthyl and phenyl intersects the A ring of the naphthyl and is, independently, —C(O)NR$^7$—, —NR$^7$C(O)—, —C(O)O—, —OC(O)—, —CH=CH—, —NR$^7$CH$_2$—, —CH$_2$NR$^7$—, —NR$^7$C(O)NR$^7$—, —NR$^7$C(O)O—, —OC(O)NR$^7$—, —NR$^7$SO$_2$O—, —OSO$_2$NR$^7$—, —OC(O)O—, —SO$_2$NR$^7$—, —NR$^7$SO$_2$—, —OSO$_2$—, or —SO$_2$O—;

each Z is independently, alkyl, substituted alkyl, cyano, halo, nitro, —$SR^{14}$, —$OR^{14}$, or —$NR^{14}_2$; and
each x and v is, independently, 0, 1, 2 or 3;
where a heteroaryl is selected from the group consisting of thienyl, furyl, pyrrolyl, indolyl isobenzofuranyl isoquinolyl, pyridyl, and quinolyl, or
a heterocyclyl is selected from the group consisting of tetrahydrofuranyl, tetrahydropyranyl, and piperidinyl,
as a single stereoisomer or mixture of stereoisomers,
or a pharmaceutically acceptable salt thereof.

25. A method of stimulating the kinase activity of the insulin receptor, comprising:
   contacting the insulin receptor, or the kinase portion thereof, with a compound of the formula:

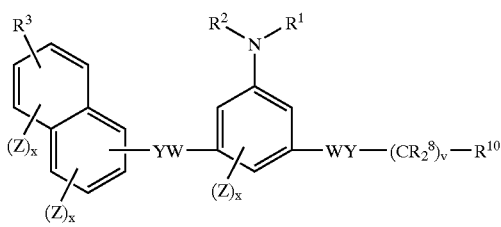

where:
$R^1$ and $R^2$ are, independently, hydrogen, alkyl, substituted alkyl, aryl, substituted aryl, —$C(O)R^4$, —$C(O)OR^4$, —$C(O)NR^4R^5$, —$S(O)_2R^4$, —$S(O)_2OR^4$, heteroaryl, substituted heteroaryl, substituted heterocyclyl, aryl(lower)alkyl, substituted aryl(lower)alkyl, heteroaryl(lower)alkyl, substituted heteroaryl(lower)alkyl, or lower alkenyl, or $R^1$ and $R^2$ together with the conjoining nitrogen are $C_5$–$C_9$ heteroaryl, $C_3$–$C_5$ heterocyclyl or both $R^1$ and $R^2$ are oxygen and together with the conjoining nitrogen forming —$NO_2$;
$R^3$ is —$SO_2OR^6$, —$C(O)OR^6$, —$SO_2NR^6_2$, —$C(O)NR^6_2$ or tetrazolyl;
   each $R^4$ and $R^5$ is, independently, hydrogen, alkyl, substituted alkyl, aryl, substituted aryl, aryl(lower)alkyl, substituted aryl(lower)alkyl substituted heteroaryl, heteroaryl, heteroaryl(lower)alkyl, substituted heteroaryl(lower)alkyl, heterocyclyl, substituted heterocyclyl, or lower alkenyl,
each $R^6$ and $R^7$ is, independently, hydrogen or lower alkyl;
each $R^8$ is, independently, hydrogen, lower alkyl, halo-lower alkyl, nitro, halo, cyano, amino, lower alkyloxy, thio, or —$C(O)OR^9$ (where $R^9$ is lower alkyl or hydrogen);
$R^{10}$ is aryl optionally substituted with lower alkyl, halo-lower alkyl halo, cyano, thio, nitro, amino, lower akyloxy, hydroxy, —$SO_2OR$, —$SO_2NR_2$, —COOR, or —$CONR_2$ (where R is hydrogen or lower alkyl);
the linker —WY— between the naphthyl and phenyl intersects the A ring of the naphthyl and is, independently, —$C(O)NR^7$—, —$NR^7C(O)$—, —$C(O)O$—, —$OC(O)$—, —CH=CH—, —$NR^7CH_2$—, —$CH_2NR^7$—, —$NR^7C(O)NR^7$—, —$NR^7C(O)O$—, —$OC(O)NR^7$—, —$NR^7SO_2O$—, —$OC(O)O$—, —$SO_2NR^7$—, —$NR^7SO_2$—, —$OSO_2$—, or —$SO_2O$—;
each Z is independently, alkyl, substituted alkyl, cyano, halo, nitro, —$SR^{14}$, —$OR^{14}$, or —$NR^{14}_2$; and
each x and v is, independently, 0, 1, 2 or 3;
where a heteroaryl is selected from the group consisting of thienyl, furyl, pyrrolyl indolyl isobenzofuranyl, isoquinolyl, pyridyl and quinolyl, or
a heterocyclyl is selected from the group consisting of tetrahydrofuranyl, tetrahydropyranyl, and piperidinyl,
as a single stereoisomer or mixture of stereoisomers,
or a pharmaceutically acceptable salt thereof,
in an amount sufficient to stimulate the kinase activity of the insulin receptor.

26. A method of activating the insulin receptor, comprising:
   contacting the insulin receptor, or the kinase portion thereof, with a compound of the formula:

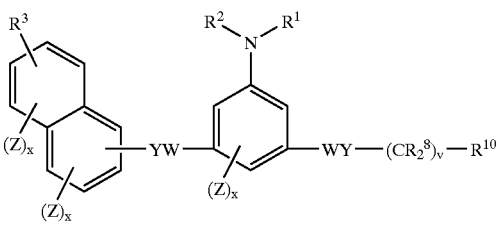

where:
$R^1$ and $R^2$ are, independently, hydrogen, alkyl, substituted alkyl aryl, substituted aryl —$C(O)R^4$, —$C(O)OR^4$, —$C(O)NR^4R^5$, —$S(O)_2R^4$, —$S(O)_2OR^4$; heteroaryl, substituted heteroaryl, heterocyclyl, substituted heterocyclyl, aryl(lower)alkyl, substituted aryl(lower)alkyl heteroaryl(lower)alkyl, substituted heteroaryl(lower)alkyl or lower alkenyl, or $R^1$ and $R^2$ together with the conjoining nitrogen are $C_5$–$C_9$ heteroaryl, $C_3$–$C_5$ heterocyclyl, or both $R^1$ and $R^2$ are oxygen and together with the conjoining nitrogen forming —$NO_2$;
$R^3$ is —$SO_2OR^6$, —$C(O)OR^6$, —$SO_2NR^6_2$, —$C(O)NR^6_2$ or tetrazolyl;
   each $R^4$ and $R^5$ is, independently, hydrogen, alkyl, substituted alkyl aryl, substituted aryl, aryl(lower)alkyl, substituted aryl(lower)alkyl, substituted heteroaryl, heteroaryl, heteroaryl(lower)alkyl, substituted heteroaryl(lower)alkyl, heterocyclyl, substituted heterocyclyl, or lower alkenyl,
each $R^6$ and $R^7$ is, independently, hydrogen or lower alkyl;
each $R^8$ is, independently, hydrogen, lower alkyl, halo-lower alkyl, nitro, halo, cyano, amino, lower alkyloxy, thio, or —$C(O)OR^9$ (where $R^9$ is lower alkyl or hydrogen);
$R^{10}$ is aryl optionally substituted with lower alkyl, halo-lower alkyl, halo, cyano, thio, nitro, amino, lower akyloxy, hydroxy, —$SO_2OR$, —$SO_2NR_2$, —COOR, or —$CONR_2$ (where R is hydrogen or lower alkyl);
the linker —WY— between the naphthyl and phenyl intersects the A ring of the naphthyl and is, independently, —$C(O)NR^7$—, —$NR^7C(O)$—, —$C(O)O$—, —$OC(O)$—, —CH=CH—, —$NR^7CH_2$—, —$CH_2NR^7$—, —$NR^7C(O)NR^7$—, —$NR^7C(O)O$—, —$OC(O)NR^7$—, —$NR^7SO_2O$—, —$OSO_2NR^7$—, —$OC(O)O$—, —$SO_2NR^7$—, —$NR^7SO_2$—, —$OSO_2$—, or —$SO_2O$—;
each Z is independently, alkyl, substituted alkyl cyano, halo, nitro, —$SR^{14}$, —$OR^{14}$, or —$NR^{14}_2$; and
each x and v is, independently, 0, 1, 2 or 3;

where a heteroaryl is selected from the group consisting of thienyl, furyl, pyrrolyl, indolyl, isobenzofuranyl isoquinolyl, pyridyl, and quinolyl or a heterocyclyl is selected from the group consisting of tetrahydrofuranyl, tetrahydropyranyl, and piperidinyl, as a single stereoisomer or mixture of stereoisomers, or a pharmaceutically acceptable salt thereof, in an amount sufficient to activate the insulin receptor.

27. A method of stimulating the uptake of glucose into cells displaying the insulin receptor, comprising:

contacting the cells with a compound of the formula:

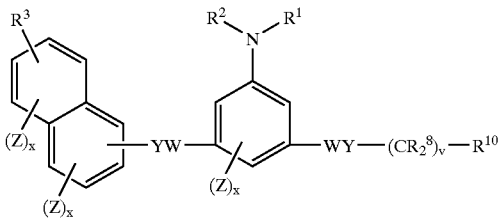

where:

$R^1$ and $R^2$ are, independently, hydrogen, alkyl, substituted alkyl, aryl substituted aryl, —C(O)$R^4$, —C(O)O$R^4$, —C(O)N$R^4R^5$, —S(O)$_2R^4$, —S(O)$_2$O$R^4$, heteroaryl, substituted heteroaryl, heterocyclyl, substituted heterocyclyl, aryl(lower)alkyl, substituted aryl(lower)alkyl heteroaryl(lower)alkyl, substituted heteroaryl(lower)alkyl, or lower alkenyl, or $R^1$ and $R^2$ together with the conjoining nitrogen are $C_5$–$C_9$ heteroaryl $C_3$–$C_5$ heterocyclyl or both $R^1$ and $R^2$ are oxygen and together with the conjoining nitrogen forming —NO$_2$;

$R^3$ is —SO$_2$O$R^6$, —C(O)O$R^6$, —SO$_2$N$R^6_2$, —C(O)N$R^6_2$ or tetrazolyl;

each $R^4$ and $R^5$ is, independently, hydrogen, alkyl, substituted alkyl, aryl, substituted aryl, aryl(lower)alkyl, substituted aryl(lower)alkyl, substituted heteroaryl, heteroaryl, heteroaryl(lower)alkyl, substituted heteroaryl(lower)alkyl, heterocyclyl, substituted heterocyclyl, or lower alkenyl, each $R^6$ and $R^7$ is, independently, hydrogen or lower alkyl;

each $R^8$ is, independently, hydrogen, lower alkyl, halo-lower alkyl nitro, halo, cyano, amino, lower alkyloxy, thio, or —C(O)O$R^9$ (where $R^9$ is lower alkyl or hydrogen);

$R^{10}$ is aryl optionally substituted with lower alkyl, halo-lower alkyl, halo, cyano, thio, nitro, amino, lower akyloxy, hydroxy, —SO$_2$OR, —SO$_2$NR$_2$, —COOR, or —CONR$_2$ (where R is hydrogen or lower alkyl);

the linker —WY— between the naphthyl and phenyl intersects the A ring of the naphthyl and is, independently, —C(O)N$R^7$—, —N$R^7$C(O)—, —C(O)O—, —OC(O)—, —CH=CH—, —N$R^7$CH$_2$—, —CH$_2$N$R^7$—, —N$R^7$C(O)N$R^7$—, —N$R^7$C(O)O—, —OC(O)N$R^7$—, —N$R^7$SO$_2$O—, —OSO$_2$N$R^7$—, —OC(O)O—, —SO$_2$N$R^7$—, —N$R^7$SO$_2$—, —OSO$_2$—, or —SO$_2$O—;

each Z is independently, alkyl, substituted alkyl, cyano, halo, nitro, —S$R^{14}$, —O$R^{14}$, or —N$R^{14}_2$; and each x and v is, independently, 0, 1, 2 or 3;

where a heteroaryl is selected from the group consisting of thienyl furyl, pyrrolyl, indolyl, isobenzofuranyl, isoquinolyl, pyridyl, and quinolyl, or a heterocyclyl is selected from the group consisting of tetrahydrofuranyl, tetrahydropyranyl, and piperidinyl, as a single stereoisomer or mixture of stereoisomers, or a pharmaceutically acceptable salt thereof, in an amount sufficient to stimulate the uptake of glucose into the cells.

28. A method of treating a disease state in a mammal selected from the group consisting of hyperglycemia, type I diabetes, and type II diabetes, comprising:

administering a therapeutically effective amount of a compound of the formula:

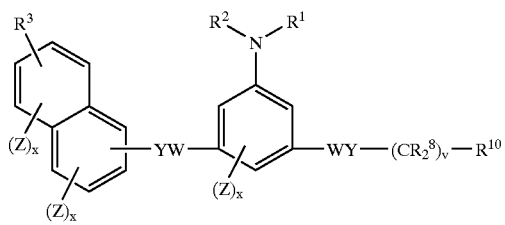

where:

$R^1$ and $R^2$ are, independently, hydrogen, alkyl substituted alkyl, aryl, substituted aryl, —C(O)$R^4$, —C(O)O$R^4$, —C(O)N$R^4R^5$, —S(O)$_2R^4$, —S(O)$_2$O$R^4$, heteroaryl, substituted heteroaryl, heterocyclyl, substituted heterocyclyl, aryl(lower)alkyl, substituted aryl(lower)alkyl, heteroaryl(lower)alkyl, substituted heteroaryl(lower)alkyl, or lower alkenyl, or $R^1$ and $R^2$ together with the conjoining nitrogen are $C_5$–$C_9$ heteroaryl, $C_3$–$C_5$ heterocyclyl, or both $R^1$ and $R^2$ are oxygen and together with the conjoining nitrogen forming —NO$_2$;

$R_3$ is —SO$_2$O$R^6$, —C(O)O$R^6$, —SC$_2$N$R^6_2$, —C(O)N$R^6_2$ or tetrazolyl;

each $R^4$ and $R^5$ is, independently, hydrogen, alkyl substituted alkyl, aryl, substituted aryl, aryl(lower)alkyl, substituted aryl(lower)alkyl, substituted heteroaryl, heteroaryl, heteroaryl(lower)alkyl, substituted heteroaryl(lower)alkyl, heterocyclyl, substituted heterocyclyl, or lower alkenyl, each $R^6$ and $R^7$ is, independently, hydrogen or lower alkyl;

each $R^8$ is, independently, hydrogen, lower alkyl, halo-lower alkyl, nitro, halo, cyano, amino, lower alkyloxy, thio, or —C(O)O$R^9$ (where $R^9$ is lower alkyl or hydrogen);

$R^{10}$ is aryl optionally substituted with lower alkyl halo-lower alkyl, halo, cyano, thio, nitro, amino, lower akyloxy, hydroxy, —SO$_2$OR, —SO$_2$NR$_2$, —COOR, or —CONR$_2$ (where R is hydrogen or lower alkyl);

the linker —WY— between the naphthyl and phenyl intersects the A ring of the naphthyl and is, independently, —C(O)N$R^7$—, —N$R^7$C(O)—, —C(O)O—, —OC(O)—, —CH=CH—, —N$R^7$CH$_2$—, —CH$_2$N$R^7$—, —N$R^7$C(O)N$R^7$—, —N$R^7$C(O)O—, —OC(O)N$R^7$—, —N$R^7$SO$_2$O—, —OSO$_2$N$R^7$—, —OC(O)O—, —SO$_2$N$R^7$—, —N$R^7$SO$_2$—, —OSO$_2$—, or —SO$_2$O—;

each Z is independently, alkyl, substituted alkyl, cyano, halo, nitro, —$SR^{14}$, —$OR^{14}$, or —$NR^{14}_2$; and each x and v is, independently, 0, 1, 2 or 3;

where a heteroaryl is selected from the group consisting of thienyl, furyl, pyrrolyl, indolyl, isobenzofuranyl, isoquinolyl, pyridyl, and quinolyl, or a heterocyclyl is selected from the group consisting of tetrahydrofuranyl, tetrahydropyranyl, and piperidinyl, as a single stereoisomer or mixture of stereoisomers, or a pharmaceutically acceptable salt thereof, to the mammal.

29. The method of claim 28, further comprising:
treating said mammal with an additional form of therapy for said disease state, where the additional form of therapy is the administration of insulin or an insulin analog.

30. The method of claim 29 where the additional form of therapy is the administration of insulin, the insulin is administered in a potentially sub-therapeutic dose, and the co-administration of the compound causes the combined dose to achieve therapeutic efficacy.

* * * * *